(12) United States Patent
Choi et al.

(10) Patent No.: US 10,709,429 B2
(45) Date of Patent: Jul. 14, 2020

(54) BIOPSY DEVICE HANDLE

(71) Applicant: Argon Medical Devices, Inc., Plano, TX (US)

(72) Inventors: Stephen Choi, Seattle, WA (US); Scott P Jarnagin, Seattle, WA (US); Adam Storey, Seattle, WA (US); Sophie Marcoux, Gainesville, FL (US)

(73) Assignee: Argon Medical Devices Inc., Plano, TX (US)

( * ) Notice: Subject to any disclaimer, the term of this patent is extended or adjusted under 35 U.S.C. 154(b) by 356 days.

(21) Appl. No.: 15/369,645

(22) Filed: Dec. 5, 2016

(65) Prior Publication Data

US 2018/0153525 A1  Jun. 7, 2018

(51) Int. Cl.
*A61B 10/02* (2006.01)

(52) U.S. Cl.
CPC ...... *A61B 10/0233* (2013.01); *A61B 10/0266* (2013.01); *A61B 2010/0208* (2013.01)

(58) Field of Classification Search
CPC .... A61B 2010/0208; A61B 2017/0046; A61B 2017/00371; A61B 10/02; A61B 10/0233; A61B 10/0266; A61B 10/0275
See application file for complete search history.

(56) References Cited

U.S. PATENT DOCUMENTS

| 5,655,542 A | 8/1997 | Weilandt |
| 5,779,647 A | 7/1998 | Chau et al. |
| 5,842,999 A | 12/1998 | Pruitt et al. |
| 5,916,175 A | 6/1999 | Bauer |
| 5,951,489 A | 9/1999 | Bauer |
| 5,976,164 A | 11/1999 | Bencini et al. |
| 5,993,399 A | 11/1999 | Pruitt et al. |
| 6,120,463 A | 9/2000 | Bauer |
| 6,126,617 A | 10/2000 | Weilandt et al. |
| 6,283,925 B1 | 9/2001 | Terwilliger |
| 6,322,523 B2 | 11/2001 | Weilandt |
| 6,358,217 B1 | 3/2002 | Bourassa |

(Continued)

FOREIGN PATENT DOCUMENTS

| WO | 2004045417 | 6/2004 |
| WO | 2006005342 | 1/2006 |

(Continued)

OTHER PUBLICATIONS

European Patent Office acting as the International Search Authority, Written Opinion of the International Searching Authority, International Patent Application No. PCT/US2017/063299, dated May 28, 2018.

(Continued)

*Primary Examiner* — Daniel L Cerioni
*Assistant Examiner* — Raymond P Dulman
(74) *Attorney, Agent, or Firm* — IpHorgan Ltd.

(57) ABSTRACT

A biopsy device handle having a biased firing mechanism activated by side and rear triggers. The firing mechanism has a longitudinally sliding deflecting portion including a post. The post is disposed within a channel and retained by a catch. The deflecting portion deflects transversely when transverse force is applied to a transverse face by the side trigger or when a longitudinal force is applied to an inclined face by the rear trigger to release the post from the catch.

13 Claims, 24 Drawing Sheets

(56) References Cited

U.S. PATENT DOCUMENTS

| | | |
|---|---|---|
| 6,626,850 B1 | 9/2003 | Chau et al. |
| 6,676,658 B2 | 1/2004 | Burbank et al. |
| 6,679,851 B2 | 1/2004 | Burbank et al. |
| 6,969,358 B2 | 11/2005 | Baltschun et al. |
| 7,022,085 B2 | 4/2006 | Cooke et al. |
| 7,156,815 B2 | 1/2007 | Leigh et al. |
| 7,329,227 B2 | 2/2008 | Schramm |
| 7,470,237 B2 | 12/2008 | Beckman et al. |
| 7,585,282 B2 | 9/2009 | Hancock |
| 7,625,347 B2 | 12/2009 | Burbank et al. |
| 8,016,856 B2 | 9/2011 | Lavelle et al. |
| 8,172,773 B2 | 5/2012 | Heske et al. |
| 8,192,369 B2 | 6/2012 | Bacon et al. |
| 8,197,419 B2 | 6/2012 | Field et al. |
| 8,262,586 B2 | 9/2012 | Anderson et al. |
| 8,277,394 B2 | 10/2012 | Hibner |
| 8,282,574 B2 | 10/2012 | Coonahan et al. |
| 8,343,070 B2 | 1/2013 | Krueger |
| 8,343,072 B2 | 1/2013 | Bacon et al. |
| 8,366,636 B2 | 2/2013 | Videbaek |
| 8,460,204 B2 | 6/2013 | Quick et al. |
| 8,506,504 B2 | 8/2013 | Field et al. |
| 8,628,482 B2 | 1/2014 | Leimbach et al. |
| 8,636,734 B2 | 1/2014 | Burbank et al. |
| 8,690,793 B2 | 4/2014 | Ranpura et al. |
| 8,734,363 B2 | 5/2014 | Bacon |
| 8,771,199 B2 | 7/2014 | Theobald et al. |
| 8,771,200 B2 | 7/2014 | Thompson et al. |
| 8,814,856 B2 | 8/2014 | Elmouelhi et al. |
| 8,968,211 B2 | 3/2015 | Ferree et al. |
| 8,979,768 B2 | 3/2015 | Privitera et al. |
| 9,060,759 B2 | 6/2015 | Williams et al. |
| 9,072,508 B2 | 7/2015 | Callede et al. |
| 9,101,347 B2 | 8/2015 | McGhie et al. |
| 9,113,856 B2 | 8/2015 | Callede et al. |
| 9,149,293 B2 | 10/2015 | Hardert et al. |
| 9,155,527 B2 | 10/2015 | Vetter et al. |
| 9,220,484 B2 | 12/2015 | Krueger |
| 9,282,948 B2 | 3/2016 | Melchiorri et al. |
| 9,332,973 B2 | 5/2016 | McWeeney et al. |
| 9,392,998 B2 | 7/2016 | Snow |
| 2003/0163152 A1 | 8/2003 | Weilandt et al. |
| 2004/0068231 A1 | 4/2004 | Blondeau |
| 2004/0158172 A1 | 8/2004 | Hancock |
| 2008/0281226 A1 | 11/2008 | Peters |
| 2011/0004120 A1 | 1/2011 | Drubetsky |
| 2014/0207021 A1 | 7/2014 | Snow |
| 2014/0276208 A1 | 9/2014 | McGhie |
| 2014/0371585 A1 | 12/2014 | Thompson et al. |
| 2015/0005663 A1 | 1/2015 | Callede et al. |
| 2015/0005670 A1* | 1/2015 | Hong .................. A61B 5/15117 600/583 |
| 2015/0201917 A1 | 7/2015 | Snow |
| 2015/0238171 A1 | 8/2015 | Shabaz |
| 2016/0249893 A1 | 9/2016 | Arnholt et al. |
| 2018/0098757 A1* | 4/2018 | Stone .................. A61B 10/0266 |

FOREIGN PATENT DOCUMENTS

| | | |
|---|---|---|
| WO | 2008106583 A1 | 9/2008 |
| WO | 2014081812 | 5/2014 |
| WO | 2014113665 | 7/2014 |

OTHER PUBLICATIONS

European Patent Office acting as the International Search Authority, Provisional Opinion Accompanying the Partial Search Result, Invitation to Pay Additional Fees, International Patent Application No. PCT/US2017/063299, dated Feb. 12, 2018, pp. 4-12.

* cited by examiner

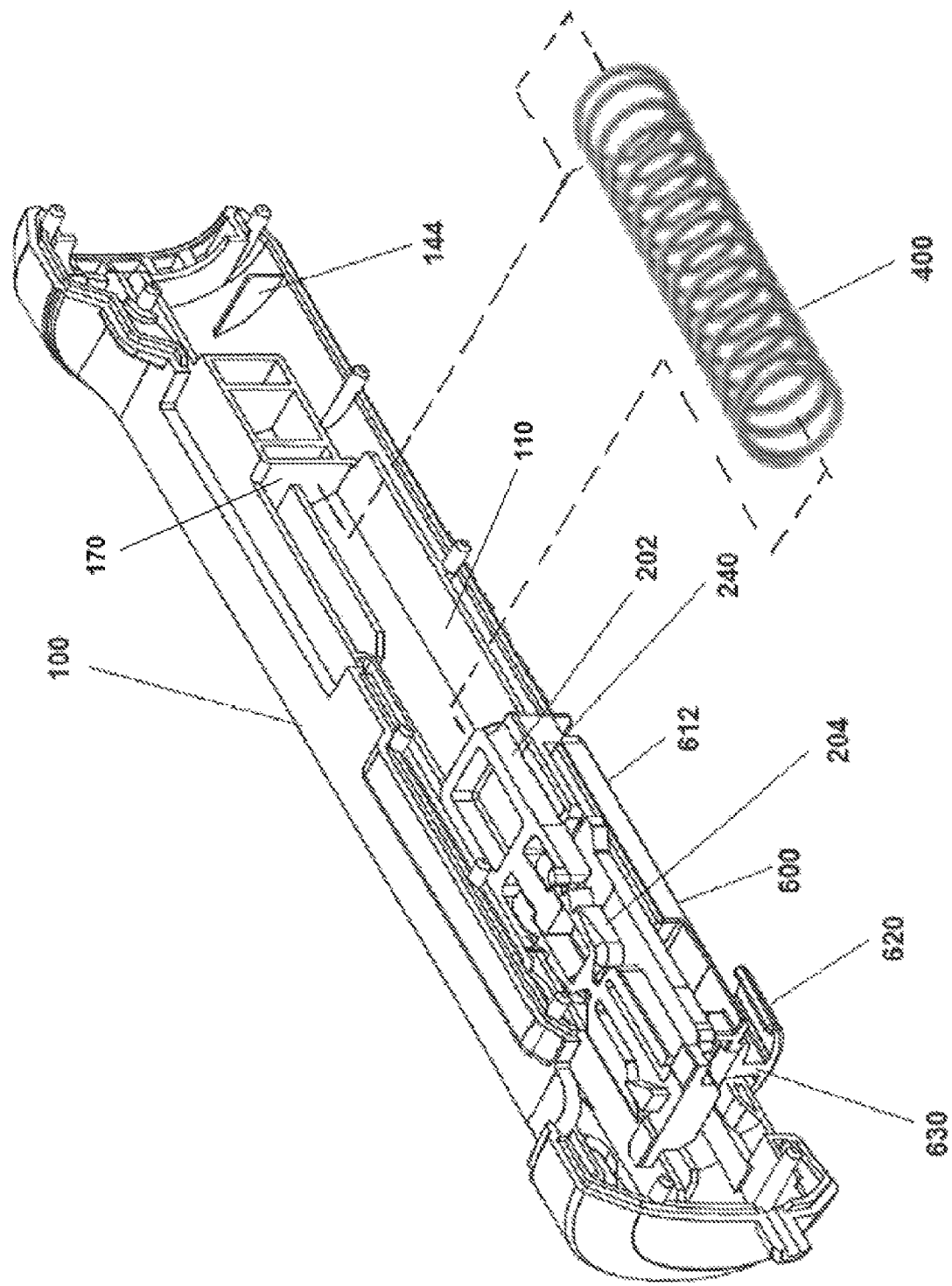

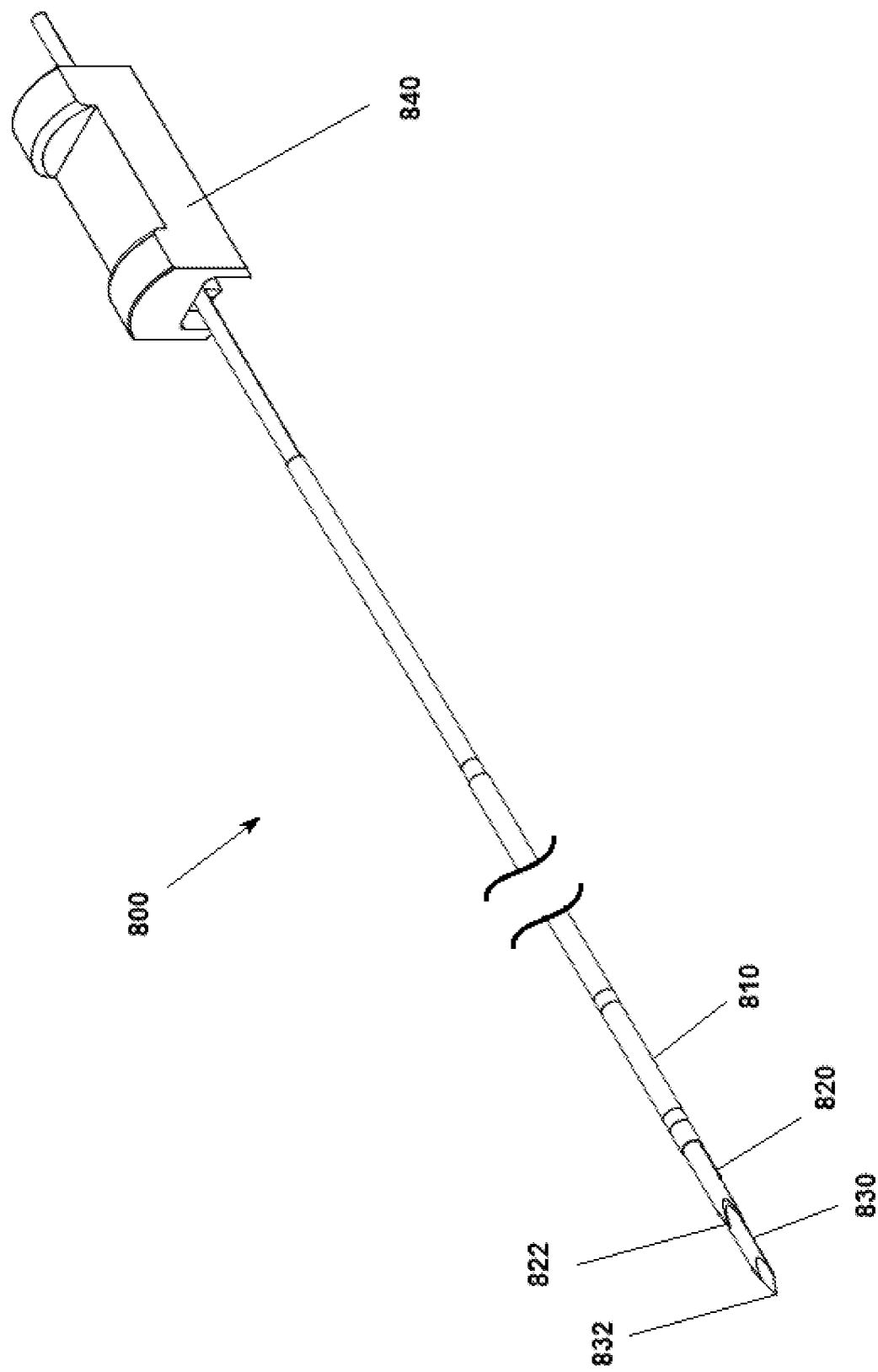

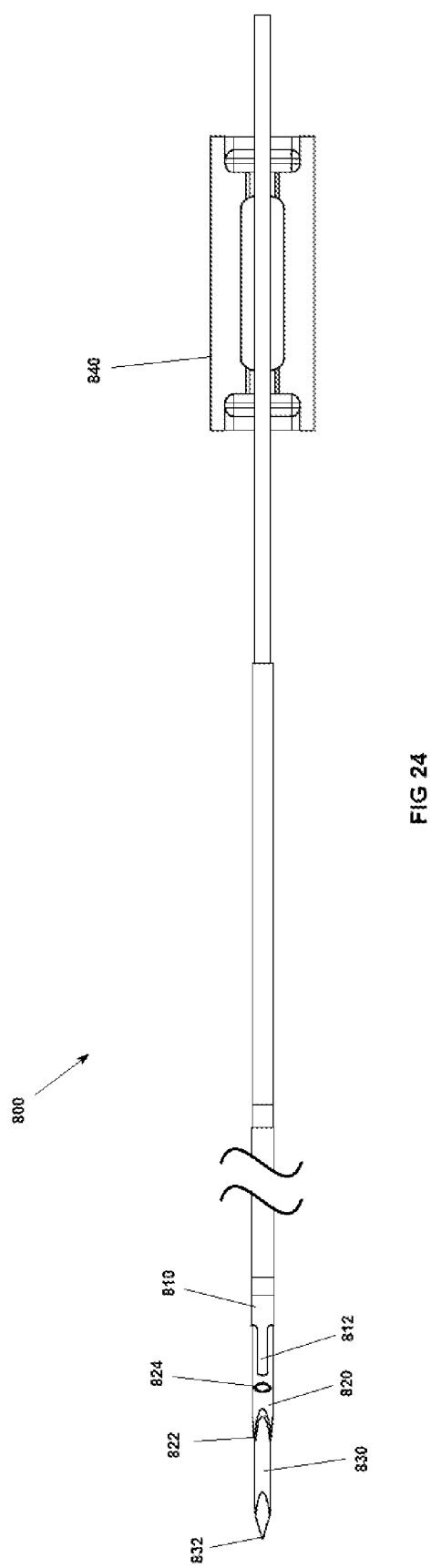

BIOPSY DEVICE HANDLE

BACKGROUND

1. Field of the Invention

The present invention relates to a biopsy device for collecting tissue samples, and particularly to a handle for a biopsy device.

2. Description of the Related Art

Biopsy is routine medical procedure to excise tissue samples for examination. Some minimally invasive techniques for biopsy procedures involve the use of automatic biopsy coring devices. Such devices typically include one or more hollow needles to cut and retain a sample of tissue, and a handle including a mechanism for advancing the needles a fixed distance into the tissue. Once such biopsy device using multiple needles is disclosed in U.S. Pat. No. 5,655,542, which is herein incorporated by reference in its entirety.

The handles of prior biopsy devices may include mechanisms for arming and firing the device, and for adjusting the depth of tissue penetration. One such prior handle is disclosed in U.S. Pat. No. 6,322,523, which is herein incorporated by reference in its entirety. However, many of those features are either difficult to operate with one hand or require awkward positioning to operate which may unnecessarily complicate a biopsy procedure.

Prior devices are typically operated by a single trigger located on either the side of the device or on the rear end of the device. U.S. Pat. No. 6,322,523 is operated by a single triggering mechanism oriented lengthwise. Such prior devices are limiting because they only allow for essentially a single hand position to operate the device, which may render the device more difficult to position for certain biopsy targets. A need therefore exists for a biopsy device having mechanisms and features capable of being operated easily with multiple hand positions.

Furthermore, the device of U.S. Pat. No. 6,322,523 is armed by operating a lever mechanism. However, the lever may be operated while the device is armed, which may inadvertently trigger the device. A need therefore exists for a biopsy device having a mechanism to prevent operation of the lever when the device is armed.

SUMMARY OF THE INVENTION

It is therefore an object of the present invention to provide a biopsy device handle comprising an elongated housing, the length of the housing defining a longitudinal axis, a carriage disposed within the housing and having a flexible abutment, a catch overlapping at least a portion of the abutment in a longitudinal direction, a first trigger disposed in the housing and movable longitudinally into the housing and contacting a portion of the flexible abutment to apply a first contact force to the abutment, a second trigger disposed in the housing and movable transversely into the housing and contacting a portion of the flexible abutment to apply a second contact force to the abutment, wherein the abutment is configured to flex away from the catch when forced by either the first or second contact force, such that the catch does not overlap a portion of the abutment.

It is also an object of the present invention to provide a biopsy device handle comprising an elongated housing, the length of the housing defining a longitudinal axis, and a carriage configured to slide generally longitudinally within the housing, the carriage having a deflecting portion configured to deflect at an angle to the longitudinal direction, wherein the deflecting portion includes a face transverse to the longitudinal axis and a flexible beam, the flexible beam configured to bend transversely when a transverse force is applied to the transverse face.

It is also an object of the present invention to provide a biopsy device handle comprising an elongated housing, the length of the housing defining a longitudinal axis, and a carriage configured to slide generally longitudinally within the housing, the carriage having a deflecting portion configured to deflect at an angle to the longitudinal direction, wherein the deflecting portion includes a protrusion having an inclined face at an angle to the longitudinal axis and a flexible beam, the flexible beam configured to bend transversely when a transverse force is applied to the inclined face.

It is also an object of the present invention to provide a biopsy device handle comprising an elongated housing, the length of the housing defining a longitudinal axis, a carriage configured to slide generally longitudinally and having a deflecting portion, the deflecting portion including an abutment and being movable between a neutral state and a deflected state, and a catcher having a catch and configured to slide generally longitudinally, wherein the protrusion and catch are at least partially aligned in a longitudinal direction when the deflecting portion is in the neutral state and the protrusion and catch are not aligned in the longitudinal direction when the deflecting portion is in the deflected state.

It is also an object of the present invention to provide a biopsy device handle comprising an elongated housing having a longitudinal slot and at least one ramp extending from an interior surface of the housing adjacent the slot, the ramp defining a first position on a proximal side of the ramp and a second position on a distal side of the ramp, and a body disposed within the housing and having a tab extending transversely through the longitudinal slot, wherein the body is configured to deflect away from the interior surface as the body is moved across the ramp between the first and second positions.

It is also an object of the present invention to provide a biopsy device handle comprising an elongated housing, an abutment configured to slide longitudinally within the housing, a biasing element configured to bias the abutment in a distal direction, and a carriage configured to slide longitudinally within the housing and having a transversely extending tab, wherein the tab is disposed distally of the abutment, and configured to contact the abutment when the carriage is moved proximally within the housing.

It is also an object of the present invention to provide a biopsy device handle comprising an elongated housing, a lever operatively linked to the housing, a lever release, the lever release configured to engage the lever when the lever release is moved to a first position and configured to disengage the lever when the lever release is moved to a second position, and a biasing element configured to bias the lever release towards the first position.

BRIEF DESCRIPTION OF THE DRAWINGS

FIG. 20B is a perspective view of the carriage assembly, stroke adjuster, and the right half of the housing of FIG. 19A, showing the stroke adjuster in a second position and the carriage assembly in a discharged state;

FIG. 23 is a perspective view of one embodiment of the needle assembly;

FIG. 24 is a bottom view of the needle assembly of FIG. 23.

DETAILED DESCRIPTION

Figure 1:
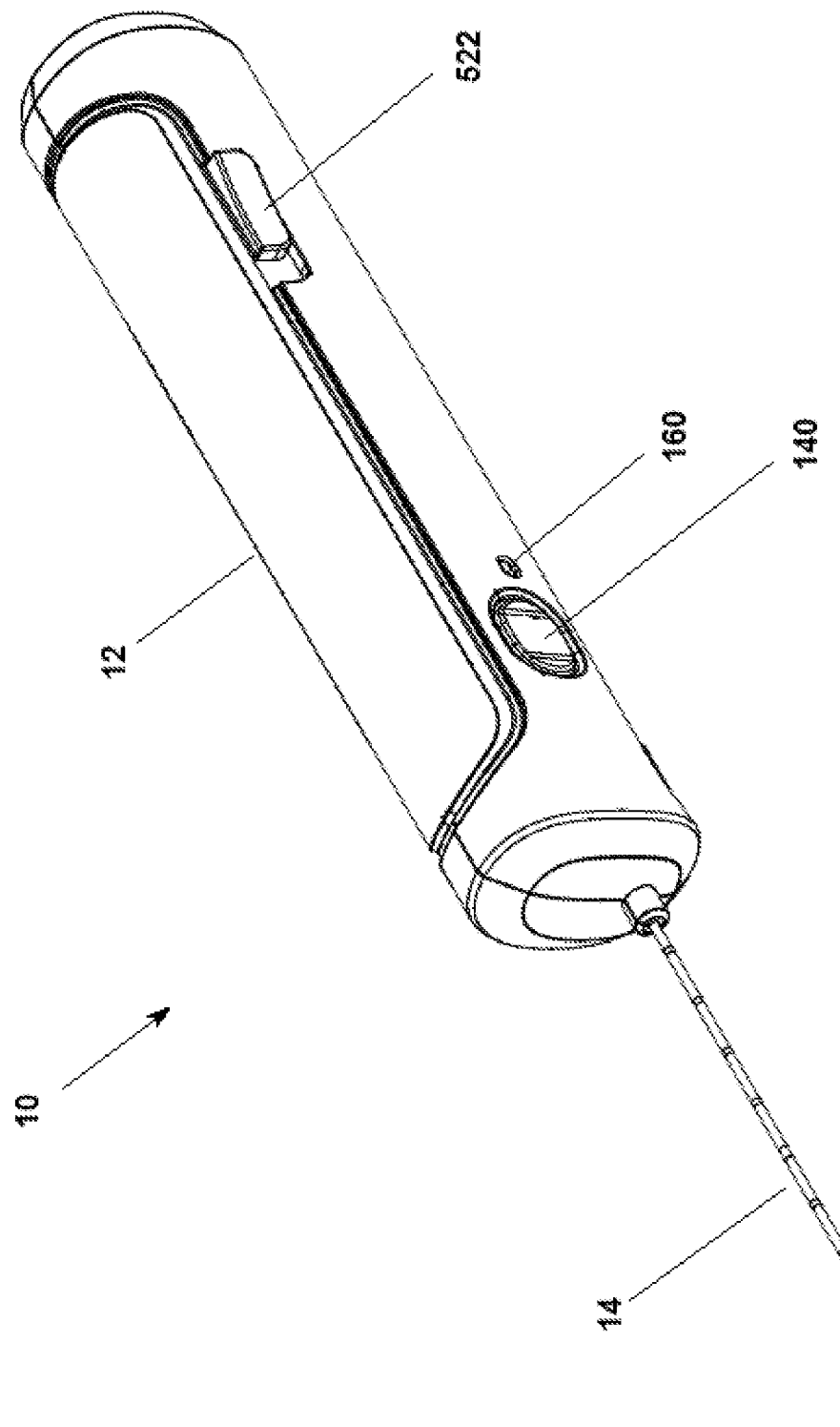
FIG. 1 is a perspective view of a biopsy device handle and needle according to the present invention.
Figure 2:
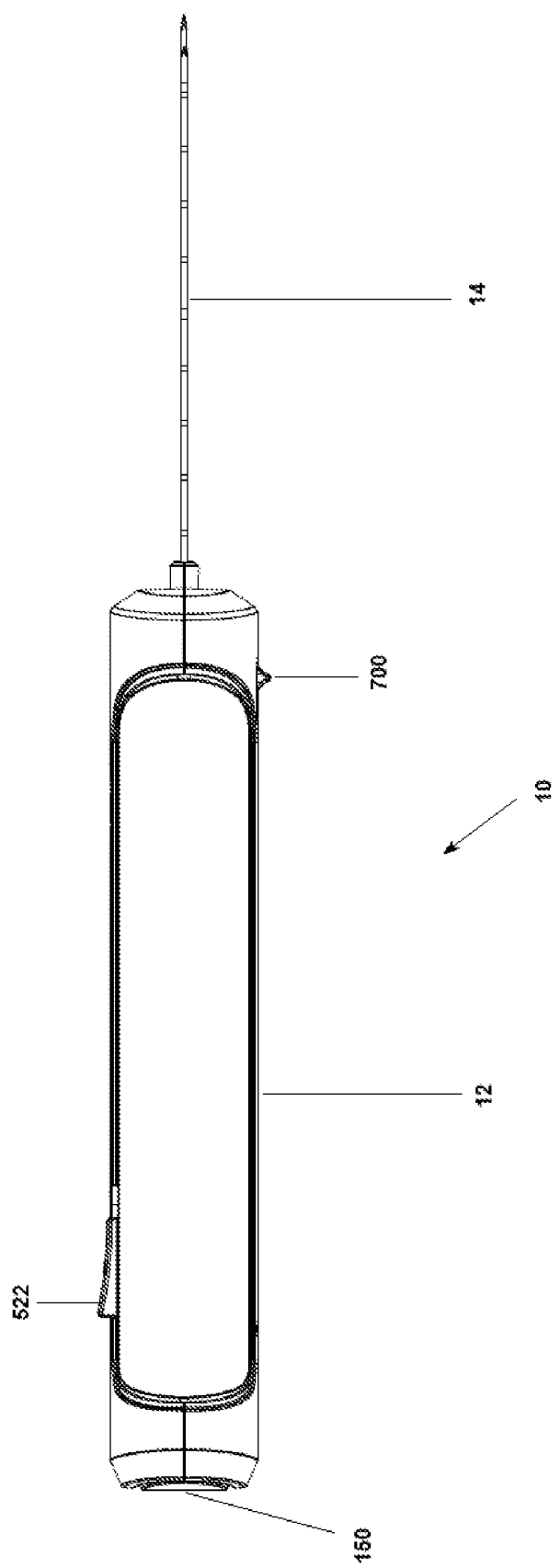
FIG. 2 is a top view of the top of the biopsy device handle and needle of FIG. 1.
Figure 3:
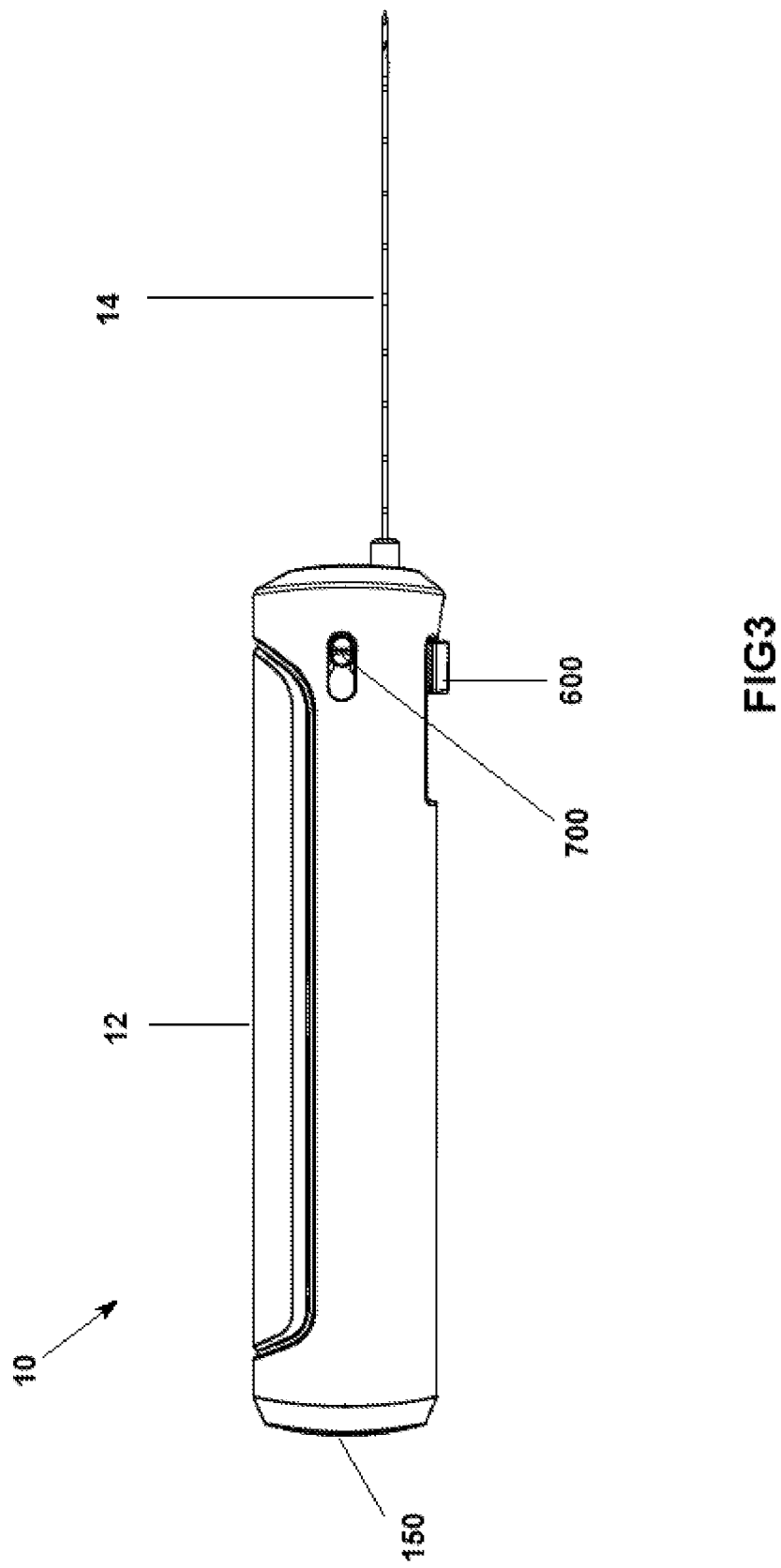
FIG. 3 is a left side view of the biopsy device handle and needle of FIG. 1

A biopsy instrument 10 according to the present invention is illustrated in FIGS. 1-7 and comprises a handle 12 and a needle 14. As used herein, the terms "proximal" and "distal" refer to an operator's point of view, with the handle 12 being at a proximal end of the device 10 and the tip of the needle 14 being at a distal end of the device 10. "Longitudinal axis" refers to the axis running the length of the device between the rear of the handle to the tip of the needle. "Lateral axis" refers to an axis running across the device from left to right. "Vertical axis" refers to an axis running across the device from top to bottom. The terms "transverse" and "transversely" refer to a direction substantially orthogonal to a previously described direction. Furthermore, although certain elements are described or depicted as being located on a particular side or end of the device or in a particular orientation, it can be appreciated that some elements may be moved or rotated while maintaining their functional relationships.

In general, the handle 12 comprises a housing 100, a carriage assembly 200, a lever assembly 300, and a first biasing element 400. The carriage assembly 200 is slidable within the housing 100 in a longitudinal direction and is biased distally by the first biasing element 400. At least a portion of the needle 14 is attached to the carriage assembly 200 and is slidable together with the carriage assembly 200. The lever assembly 300 is operatively connected to the carriage assembly 200 such that when the lever 310 is operated, the carriage assembly 200 is retracted proximally into the housing, compressing the first biasing element 400, and arming the device for sampling. When the device 10 is activated, the carriage assembly 200 is released from the lever assembly 300 and the carriage assembly 200 is advanced distally by the first biasing element 400. The portions of the needle 14 attached to the carriage assembly 200 are advanced distally into the target tissue to cut a tissue sample for retrieval.

Figure 8:
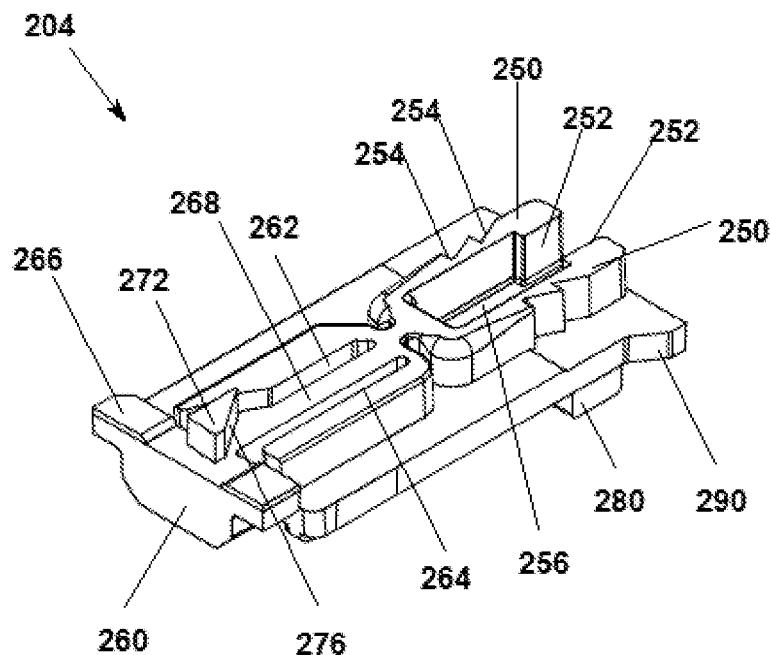
FIG. 8 is a perspective view of the front carriage according to one embodiment of the biopsy device handle.
Figure 9:
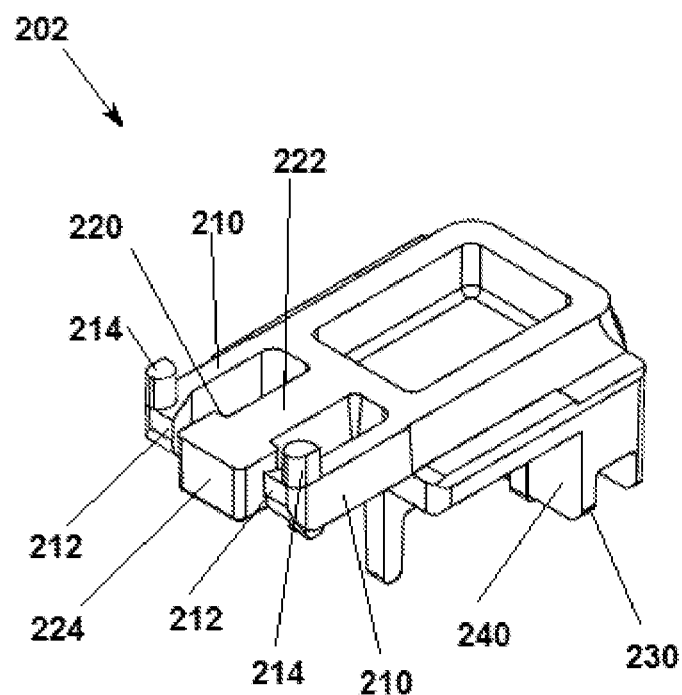
FIG. 9 is a perspective view of the rear carriage according to one embodiment of the biopsy device handle.

FIGS. 8-9, 10A-B, and 11A-B illustrate one embodiment of the carriage assembly 200. The carriage assembly 200 comprises a rear carriage 202 and a front carriage 204. As shown in FIG. 9, the rear carriage 202 includes a pair of prongs 210 extending from a distal end of the rear carriage 202 and a tab 220 extending between the two prongs 210. The prongs 210 are sufficiently flexible to flex laterally outwardly and away from the tab 220. Poles 214 project upwardly from the ends of prongs 210. Flanges 230 are formed on opposite sides of the rear carriage 202 and configured to rest upon carriage rails 110 formed in the housing 100.

The front carriage 204 includes a pair of tines 250 extending from a proximal end of the front carriage. The tines 250 define a cavity 256 configured to receive the tab 220. In at least one embodiment, illustrated in FIG. 8, the tab 220 includes a stem 222 and a head 224 wider than the stem 222. The tines 250 are spaced apart approximately the width of the head 224, and include inwardly facing tips 252 defining a space approximately the width of the stem 222. As the front carriage 204 and rear carriage 202 are joined, the tab 220 is inserted between the tines 250. Once the head 224 has been inserted past the tips 252, the tab 220 is secured. The front carriage 204 also includes a pair of flanges 280 formed on opposite sides and configured to rest upon the carriage rails 110.

Figure 10A:
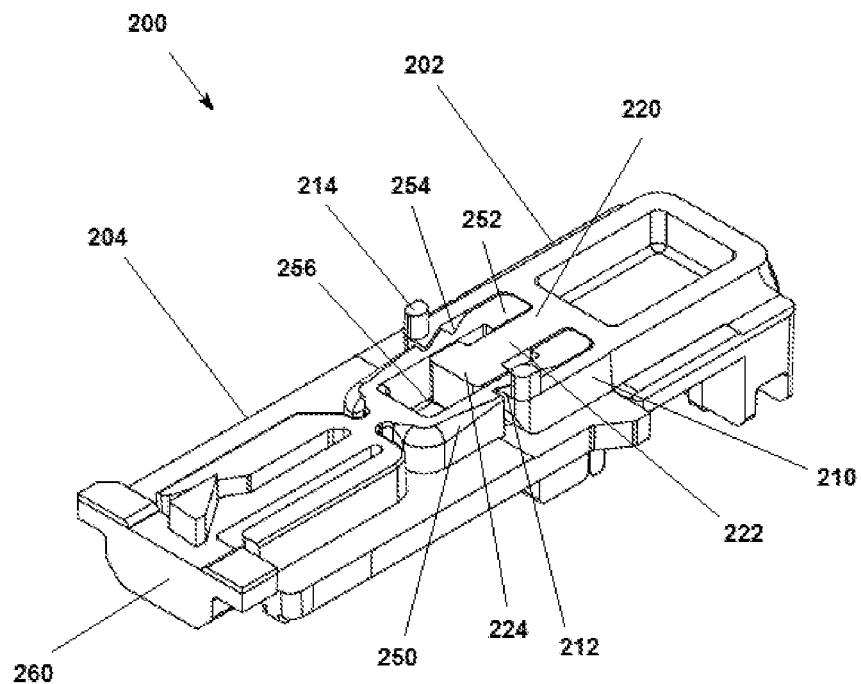
FIG. 10A is a perspective view of the carriages of FIGS. 8-9, showing the carriages assembled in a charged state.
Figure 10B:
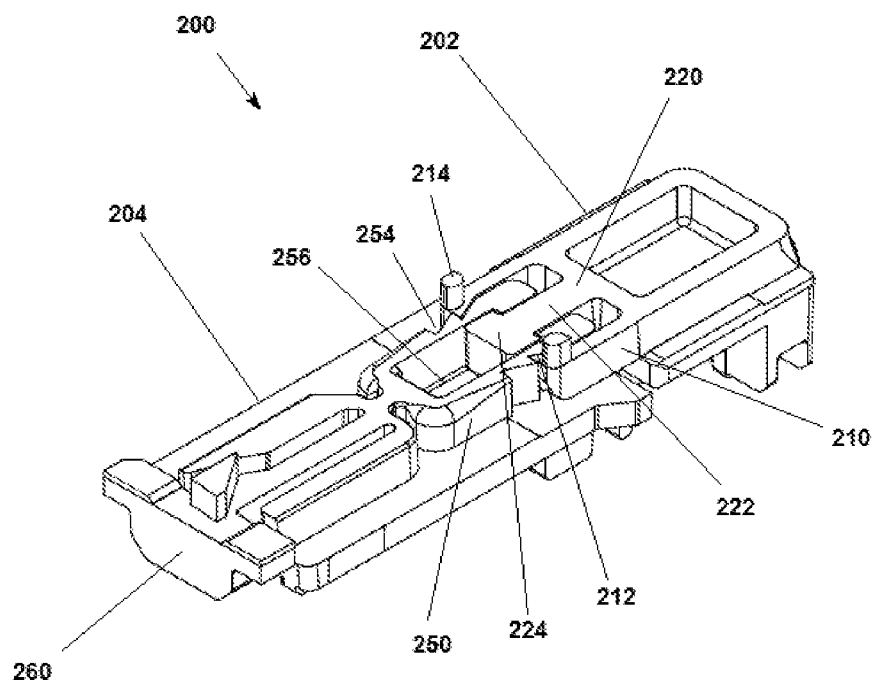
FIG. 10B is a perspective view of the carriages of FIGS. 8-9, showing the carriages assembled in an discharged state.
Figure 11A:
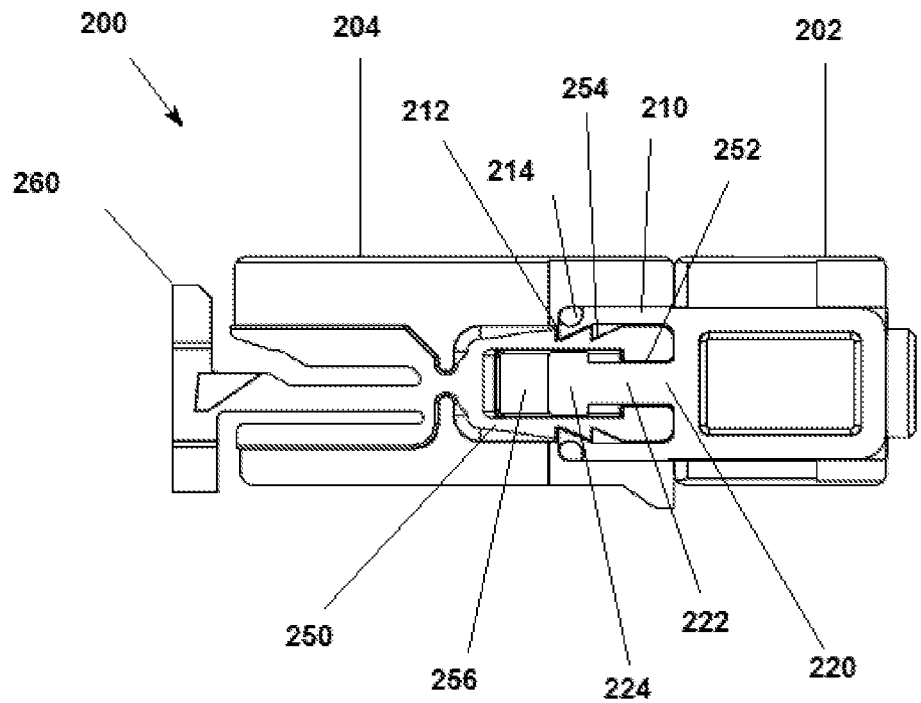
FIG. 11A is a top view of the carriage assembly of FIG. 10A.
Figure 11B:
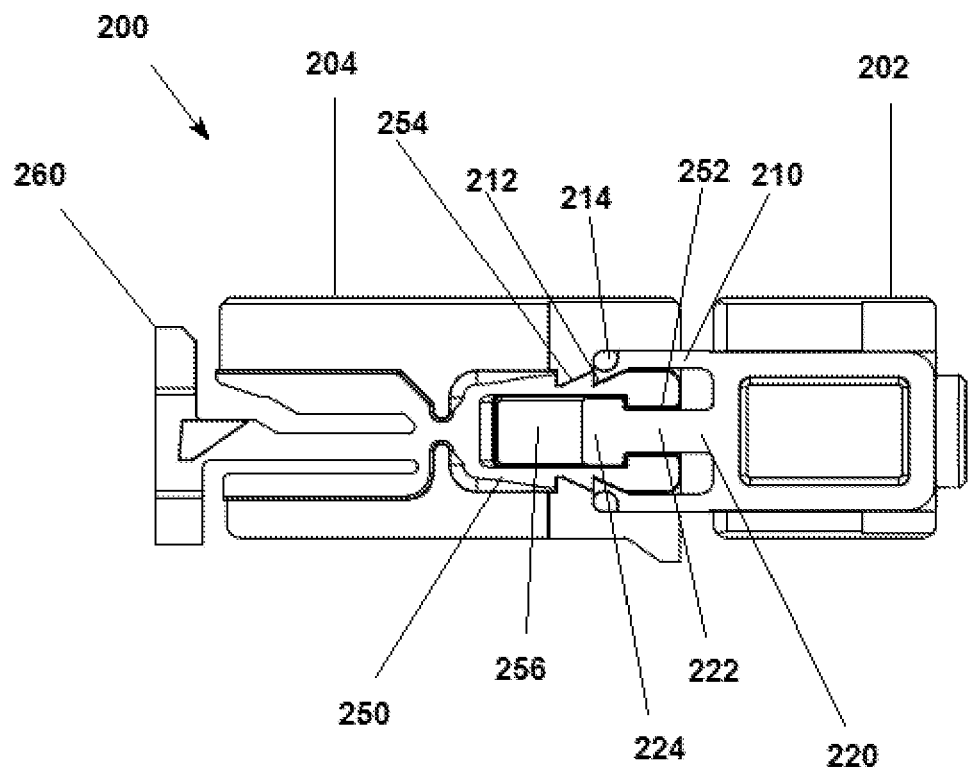
FIG. 11B is a top view of the carriage assembly of FIG. 10B.

In at least one embodiment, the cavity 256 is longer than the head 224, enabling the rear carriage 202 to slide relative to the front carriage 204 while the two pieces are mated, as illustrated in FIGS. 10A-B. In this embodiment, prongs 210 are coplanar with the tines 250, but are partially overlapping the tines 250 when viewed from the top of the device, as shown in FIGS. 11A-B. The tines 250 also include a plurality of serrations 254 along their outer edges. Each of the prongs 210 also includes an inward-facing projection 212, which extends sufficiently to engage the serrations 254. As the tab 220 is moved within the cavity 256 while the front carriage 204 and rear carriage 202 are mated, the prongs 210 are flexed outward slightly, and the projections 212 slide across the serrations 254. Preferably, the serrations 254 are generally triangular in shape, having a steeper slope on the distal side than on the proximal side. In the preferred embodiment, the asymmetrical slope of the serrations 254 require less force to pull the rear carriage 202 and front carriage 204 apart than it does to push them together, providing a ratcheting effect.

During arming of the device, the mated rear carriage 202 and front carriage 204 are pulled proximally against the first biasing element 400. The first biasing element 400 is preferably a helical spring, although other compressible spring-like elements are within the scope of the invention. In at least one embodiment, the first biasing element extends between a biasing wall 170 near a proximal end of the housing 100 and a proximal face of the rear carriage 202. In other embodiments, the first biasing element 400 may extend between the biasing wall 170 and the front carriage 204. In still further embodiments, the first biasing element 400 may surround a portion of the needle assembly 800.

During the arming process, the prongs 210 are flexed apart to allow the projections 212 to pass over the steep inclines of the serrations 254 and bring the carriages 202, 204 together. In at least one embodiment, the prongs 210 are forced apart as a pair of inclines 338 are advanced between the poles 214. When the front carriage 204 and rear carriage 202 are brought together, the carriage assembly 200 is in a charged state 922.

When the device is fired, both carriages 202, 204 move together in a distal direction until a distal face 240 of the rear carriage 202 impacts an end face 614. As shown in FIGS. 19A-B and 20A-B, the front carriage 204 travels a short distance relative to the rear carriage 202 as the tab 220 moves within the cavity 256 and the serrations 254 are moved relative to the projections 212, transitioning to a discharged state 924. Preferably, the embodiment of the device shown in FIGS. 19A-B and 20A-B is used with a nested needle assembly 800, where different portions of the needle assembly 800 are attached to the front carriage 204 and rear carriage 202 to allow the portions of the needle assembly 800 to move relative to each other.

In some embodiments, the end face 614 is movable to adjust the depth of penetration of the device. In the embodiment shown in FIGS. 19A-B and 20A-B, a stroke adjuster 600 comprises a main body 610 and a slider 620 attached to the bottom surface of the main body 610 by a neck 630. A pair of arresting arms 612 extend proximally from the main body 610 and each include an end face 614. The main body 610 is disposed inside the housing 100, and the neck 630 extends downward through a longitudinal slot 120 formed in a bottom surface of the housing 100. On each side of the longitudinal slot 120, the interior surface of the housing 100 is provided with a plurality of ramps 130 in a row extending away from the interior surface. The main body 610 may include a pair of skids 616 projecting downwardly and configured to engage the ramps 130. The ramps 130 are configured to resist longitudinal movement of the skids 616 in the distal direction. Preferably, the ramps 130 are inclined more steeply on the proximal side than on the distal side. An upwardly transverse force may be applied to the slider 620 to lift the skids 616 clear of the ramps 130 and enable the stroke adjuster 600 to be manipulated longitudinally.

In one embodiment, the housing 100 is provided with three pairs of ramps 130 defining three adjustable positions. However, other numbers of ramps 130 may be used to define the desired number of adjustable positions. The numbers of necks 630, longitudinal slots 120, and rows of ramps 130 may be modified without departing from the scope of the invention; for example, the housing may be provided with a single row of ramps and a longitudinal slot on each side of the ramps, and the stroke adjustor may be provided with two necks, each neck extending through one of the longitudinal slots.

Figure 19A:
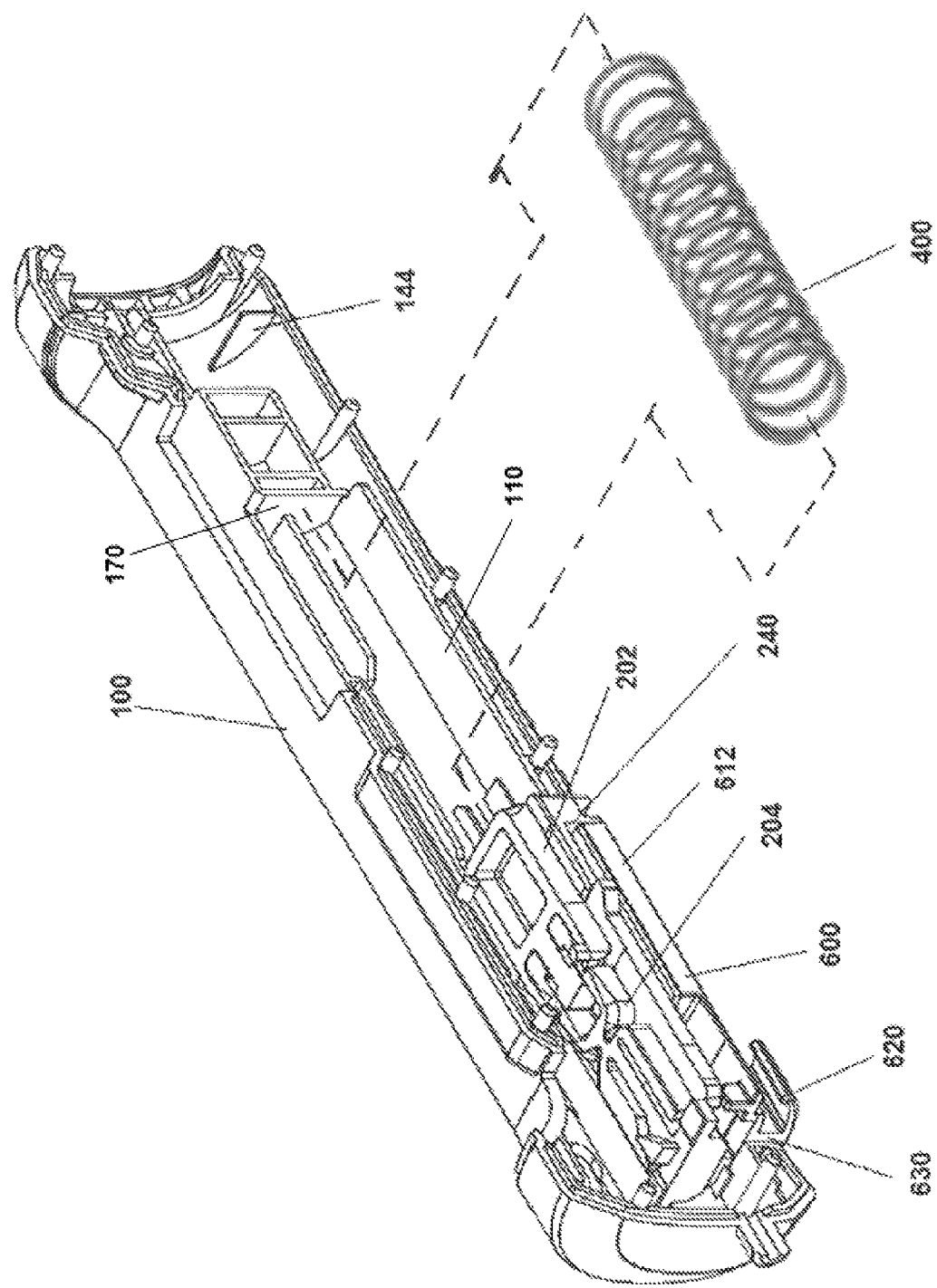
FIG. 19A is a perspective view of the carriage assembly, stroke adjuster, and the right half of the housing according to one embodiment of the present invention, showing the stroke adjuster in a first position and the carriage assembly in a charged state.
Figure 19B:
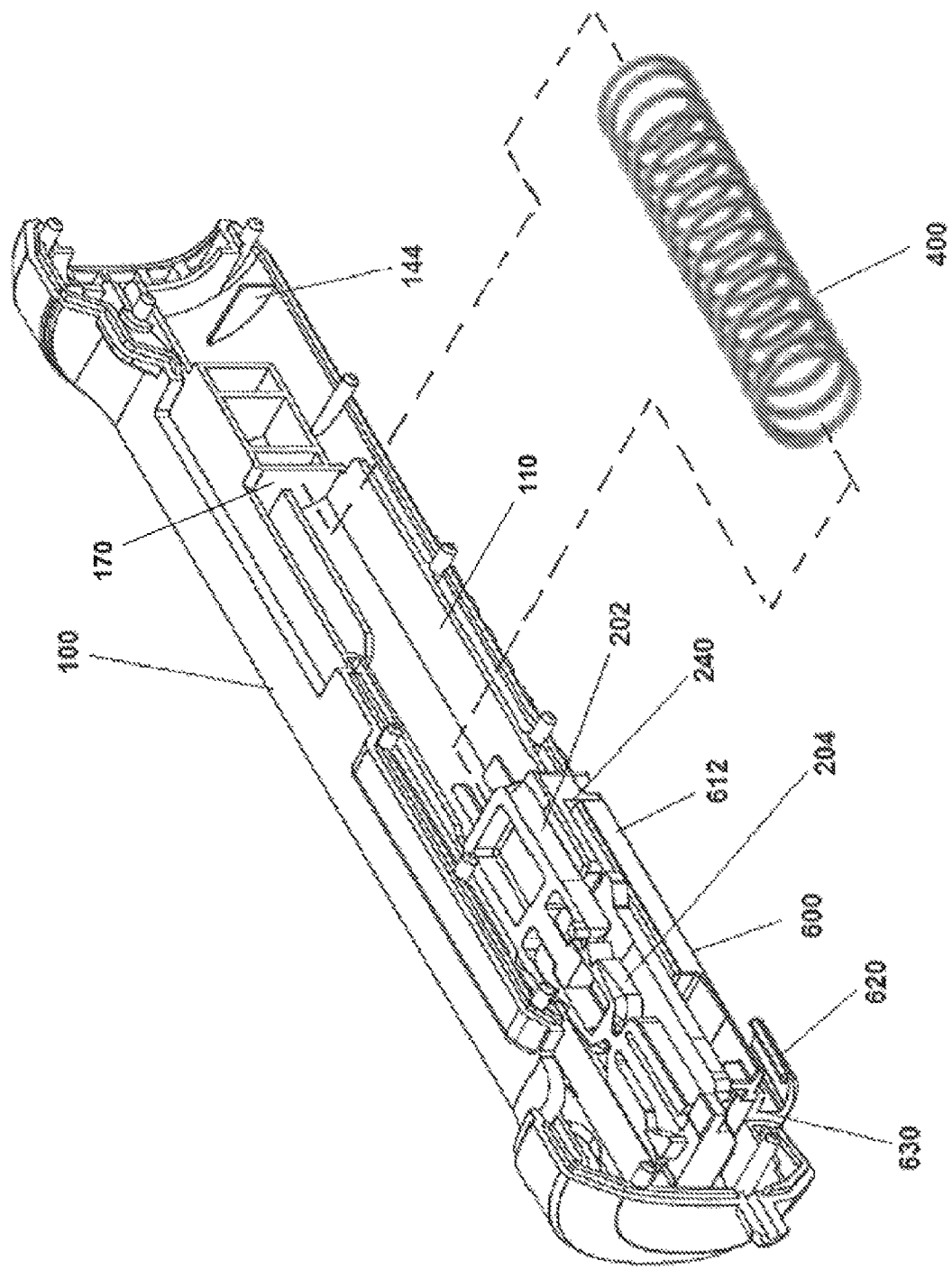
FIG. 19B is a perspective view of the carriage assembly, stroke adjuster, and the right half of the housing of FIG. 19A, showing the stroke adjuster in a first position and the carriage assembly in a discharged state.
Figure 20A:
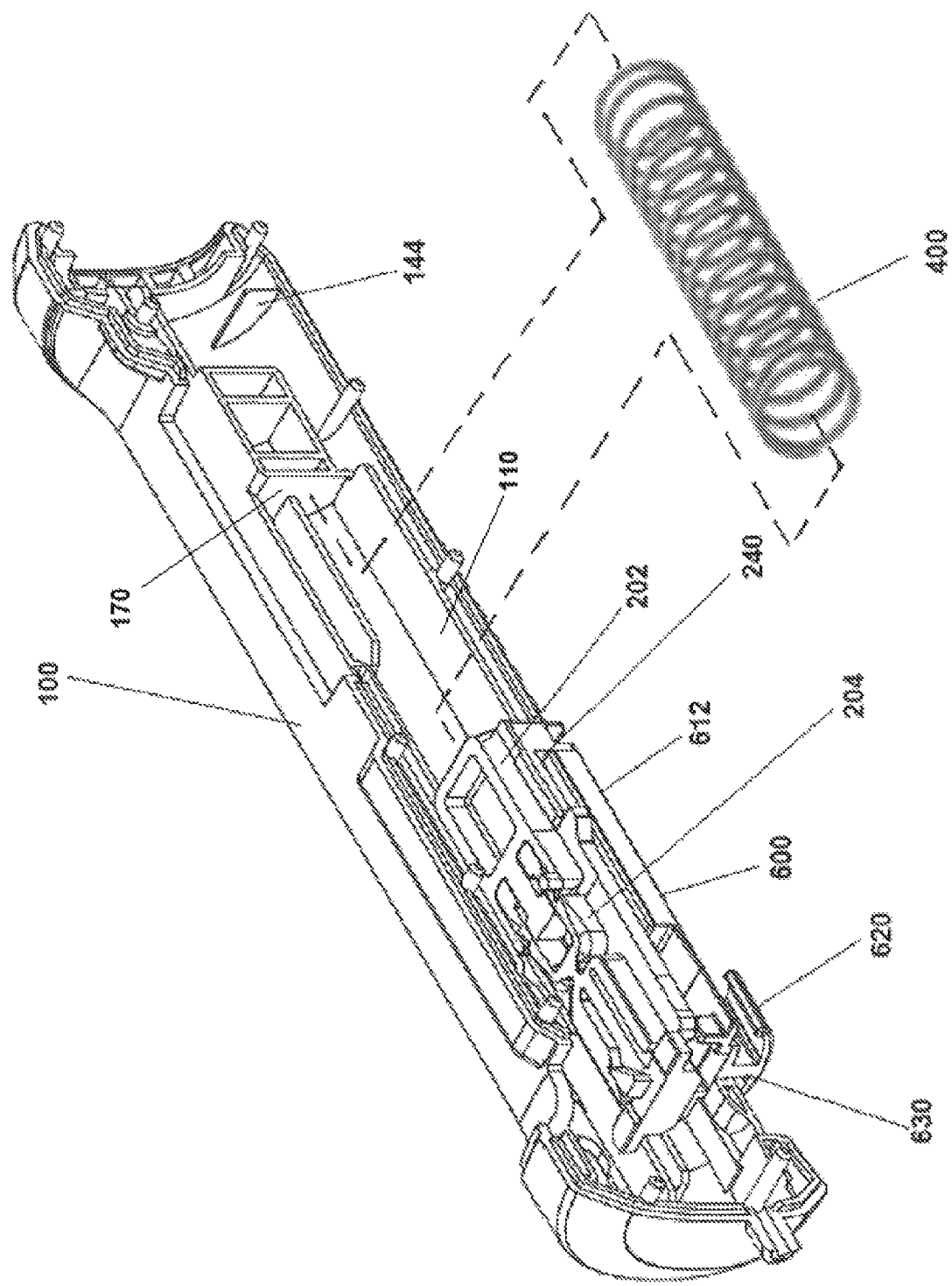
FIG. 20A is a perspective view of the carriage assembly, stroke adjuster, and the right half of the housing of FIG. 19A, showing the stroke adjuster in a second position and the carriage assembly in a charged state.

As the device is fired, the carriage assembly 200 is forced to the distal end of the housing 100. As the distal face 240 of the rear carriage 202 impacts the end face 614 at the end of the arresting arms 612, the rear carriage 202 is arrested. The ramps 130 are configured to be sufficiently steep to prevent the skids 616 from slipping against the ramps 130 due to the impact force of the rear carriage 202 contacting the end face 614. FIGS. 19A-B show the stroke adjuster positioned between the first ramp and the end of the housing 100. FIGS. 20A-B show the stroke adjuster 600 positioned between the first ramp and second ramp. Since the stroke adjuster 600 is movable between a plurality of positions, the distance traveled by the carriage assembly 200 is thereby also adjusted accordingly. In embodiments where a needle cannula is fixed to the one or both carriages 202, 204, the depth of penetration is thereby also adjusted.

In some embodiments, the needle assembly 800 comprises an outer cannula 810, an inner cannula 820, and a stylet 830 positioned coaxially, for example the needle as disclosed in U.S. Pat. No. 5,655,542. FIGS. 23-24 illustrate a multiple-cannula needle according to one embodiment of the present invention. The stylet 830 terminates in a sharp tip 832. The inner cannula 820 surrounds and is coaxial with the stylet 830. The inner cannula 820 terminates in a cutting tip 822 to cut a generally cylindrical sample of tissue. As shown in FIG. 24, the inner cannula 820 also includes an opening 824 proximal to the tip 822. The outer cannula 810 surrounds and is coaxial with the inner cannula 820. A finger 812 extends distally from the end of the outer cannula 810 and is angled toward the longitudinal axis. The finger 812 has a width less than the width of the opening 824. In this embodiment, the stylet 830 does not move with respect to the housing 100. Preferably, a proximal end of the stylet 830 is secured in a clump 840, which rests in a groove in the housing 100. The inner cannula 820 is fixed to the rear carriage 202. The outer cannula 810 is fixed to the front carriage 204.

During insertion of the needle 14, the innermost stylet 830 is extended beyond the tips of the inner cannula 820 and outer cannula 810. When the device 10 is activated, the inner cannula 820 and outer cannula 810 are advanced together distally beyond the tip of the stylet 830. As the inner cannula 820 penetrates the tissue, the cutting tip 822 cores a sample of tissue. Once the inner cannula 820 has reached the intended depth into the tissue, the inner cannula 820 is prevented from further penetrating the tissue. When used with the carriage assembly 200 shown in FIGS. 19A-B and 20A-B, the cutting depth is reached when the rear carriage 202 contacts the end face 614. The outer cannula 810 continues to travel a short distance with respect to the inner cannula 820 as the front carriage 204 transitions to the discharged state 924. As the outer cannula 810 advances, the finger 812 inserts into the opening 824 of the inner cannula 820 to cut the tissue sample transversely. Because the finger 812 remains inserted into the end of the inner cannula 820, the tissue sample is retained in the inner cannula 820, and the entire needle assembly 800 is withdrawn.

Although a needle assembly having two cannulas is preferred, some embodiments may use other types of needles including single cannula needles. In those embodiments, the carriage assembly 200 may comprise only a single carriage. A single carriage design does not become charged or discharged because there are no moving parts. Accordingly, the single carriage may omit features facilitating charging and discharging such as the prongs 210, the tab 220, and the tines 250.

Figure 12:
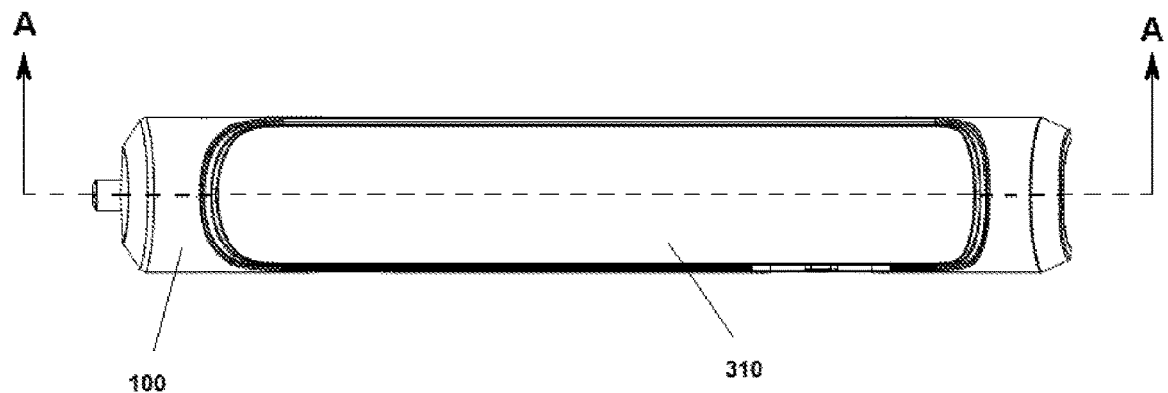
FIG. 12 is a top view of the lever assembly and housing according to one embodiment of the biopsy device handle in a closed position.
Figure 12A:
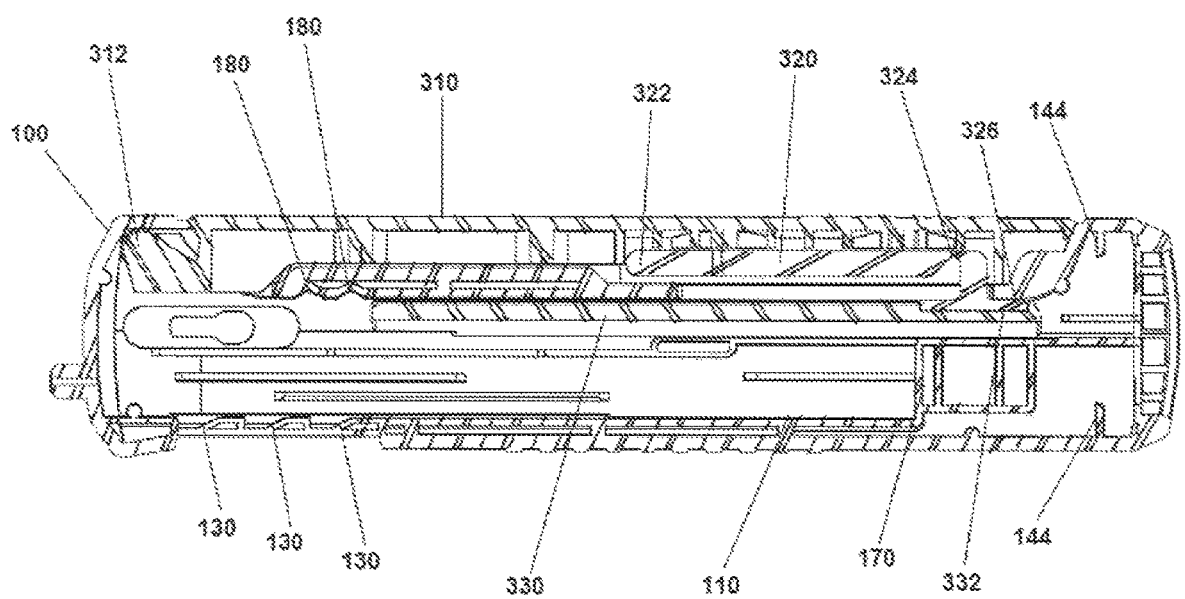
FIG. 12A is a cross-sectional view along lines A-A in FIG. 12.
Figure 13:
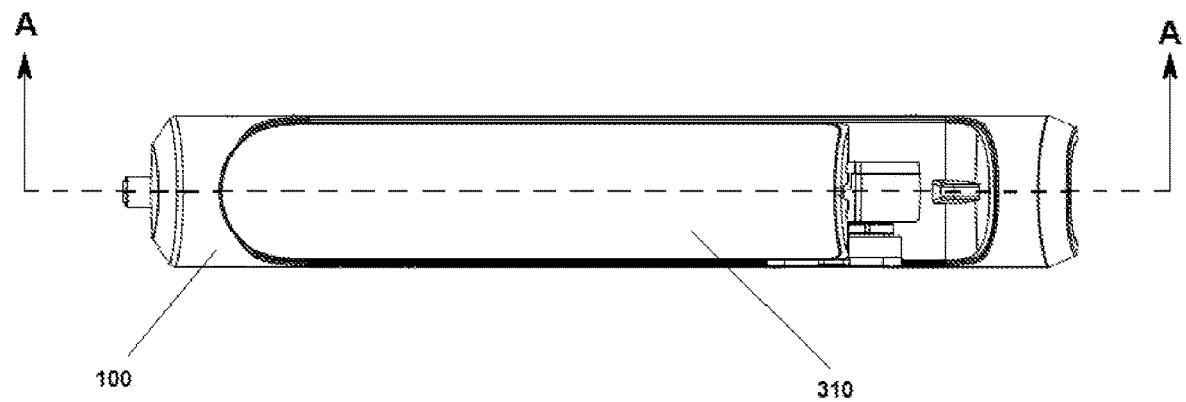
FIG. 13 is a top view of the lever assembly and housing of FIG. 12 in an open position.
Figure 13A:
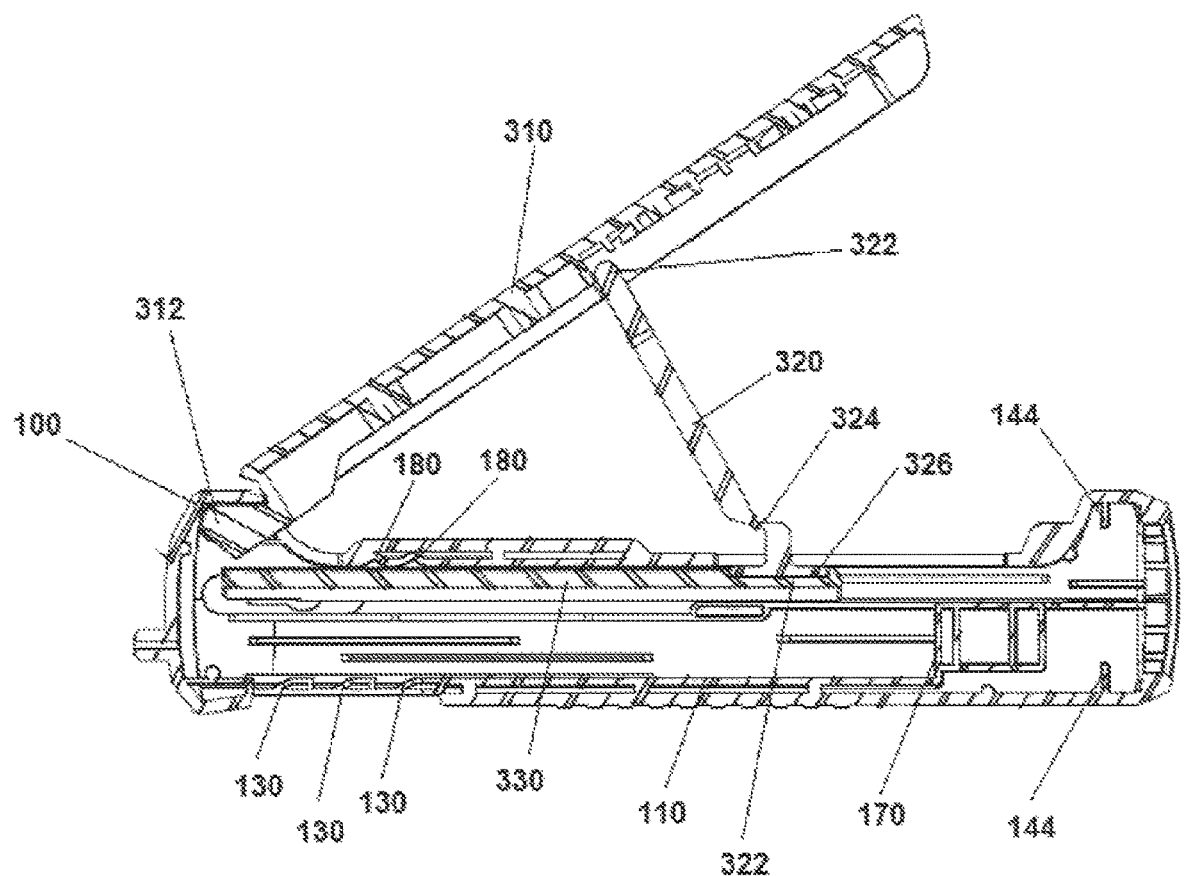
FIG. 13A is a cross-sectional view along lines A-A in FIG. 13.
Figure 14:
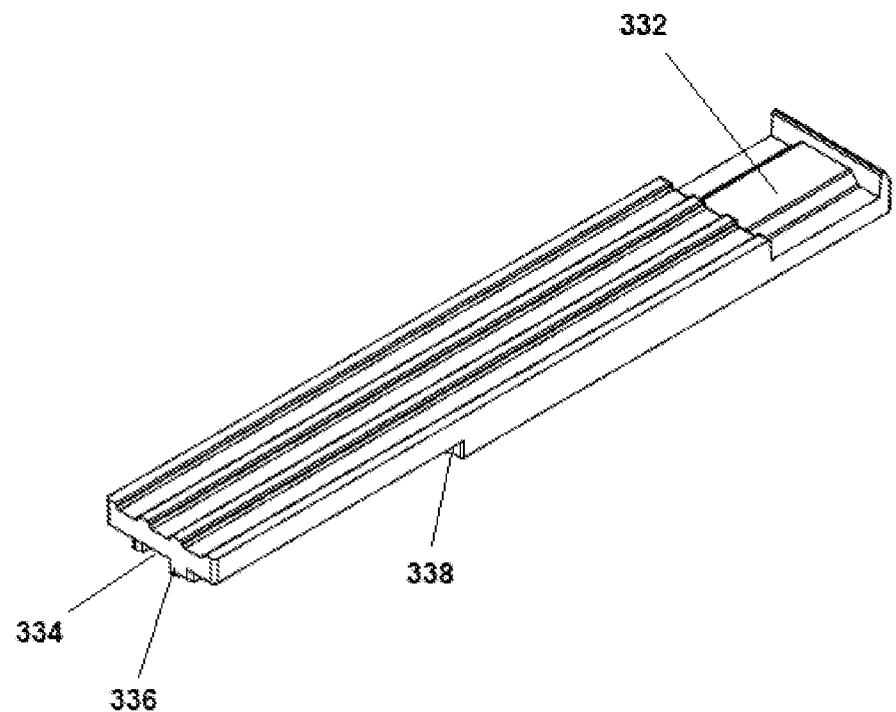
FIG. 14 is a perspective view of the catcher according to one embodiment of the biopsy device handle.
Figure 15:
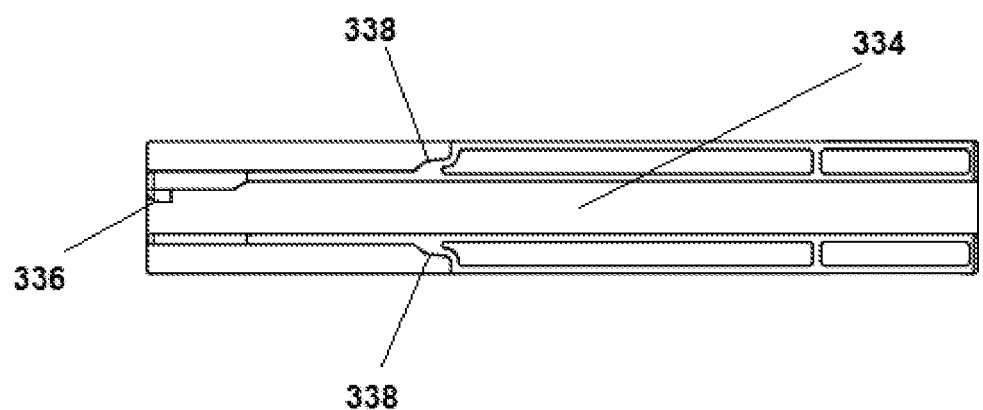
FIG. 15 is a bottom view of the catcher of FIG. 14.
Figure 16:
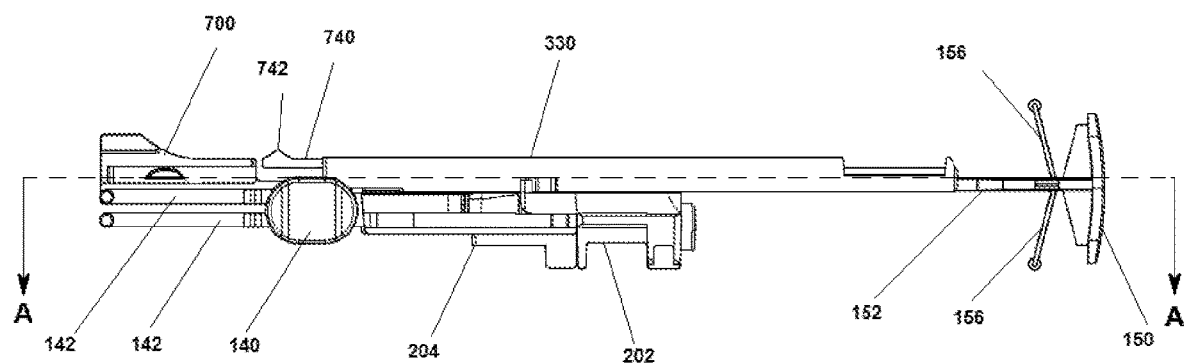
FIG. 16 is a right side view of the carriage assembly, catcher, side trigger, rear trigger, and safety according to one embodiment of the present invention, showing the safety in a locked position.
Figure 16A:
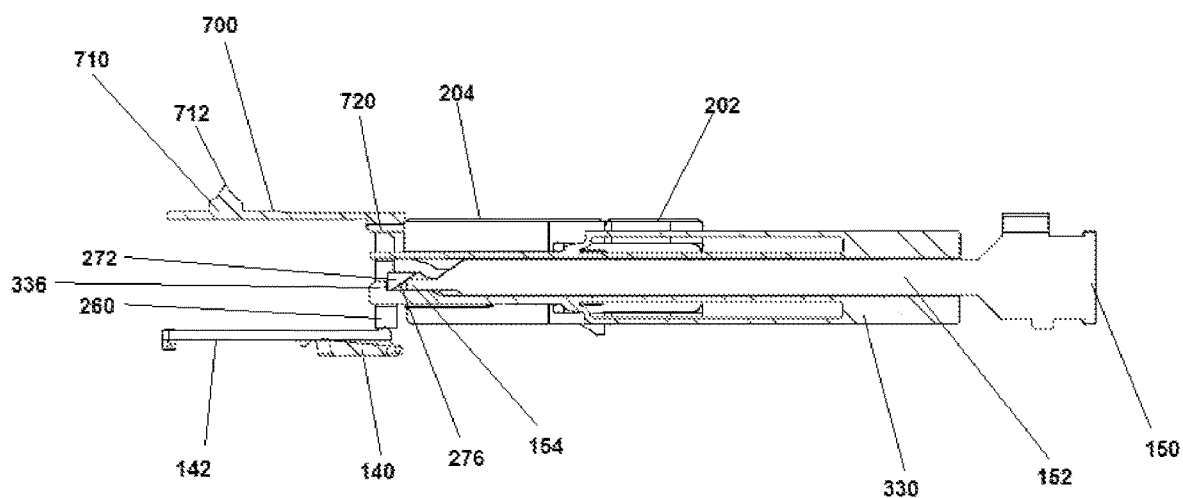
FIG. 16A is a cross-sectional view along lines A-A in FIG. 16.

In order to prepare the device for activation, the carriage assembly 200 is withdrawn proximally against the first biasing element 400 using the lever assembly 300. As shown in FIGS. 12A and 13A, the lever assembly 300 comprises a lever 310, a linkage 320, and a catcher 330. The lever 310 is attached to the housing 100 by a first hinged connection 312 at the distal end. Preferably the first hinged connection 312 is a T-shaped hinge, however other types of hinges may be used. The linkage 320 is attached to the lever 310 by a second hinged connection 322 near the middle of the lever 310 and extends proximally. Preferably the second hinged connection 322 is also a T-shaped hinge, however types of hinges may be used. The linkage 320 includes a foot 326 attached to the main body of the linkage by a third hinged connection 324. The third hinged connection 324 is preferably a living hinge, although other types of hinges are within the scope of the invention.

The catcher 330 includes a footplate 332 in the top surface of the catcher 330 at a proximal end, which is configured to seat the foot 326. A shallow longitudinal channel 334 is formed in a bottom surface of the catcher 330 to a first depth. At a distal end of the catcher 330, a transversely projecting catch 336 extends from a side wall of the channel 334.

Figure 17:
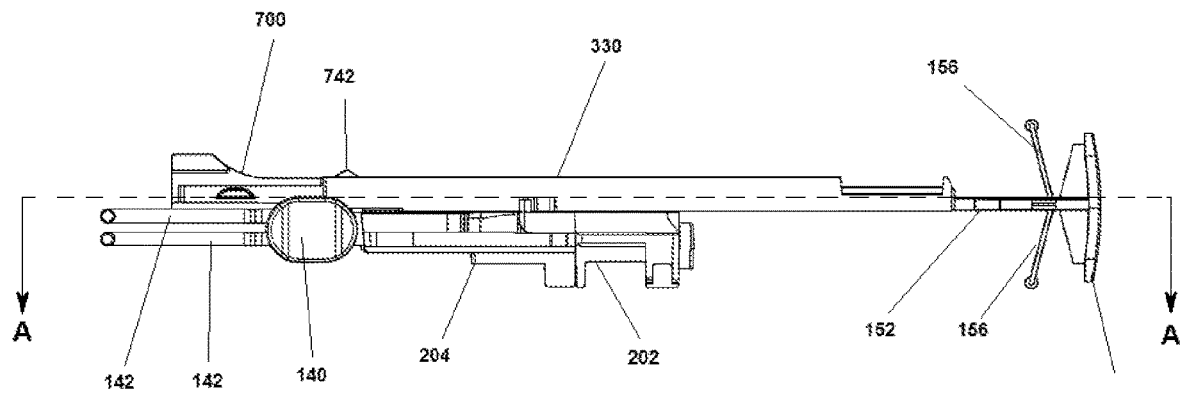
FIG. 17 is a right side view of the carriage assembly, catcher, side trigger, rear trigger, and safety of FIG. 16, showing the safety in an unlocked position.
Figure 17A:
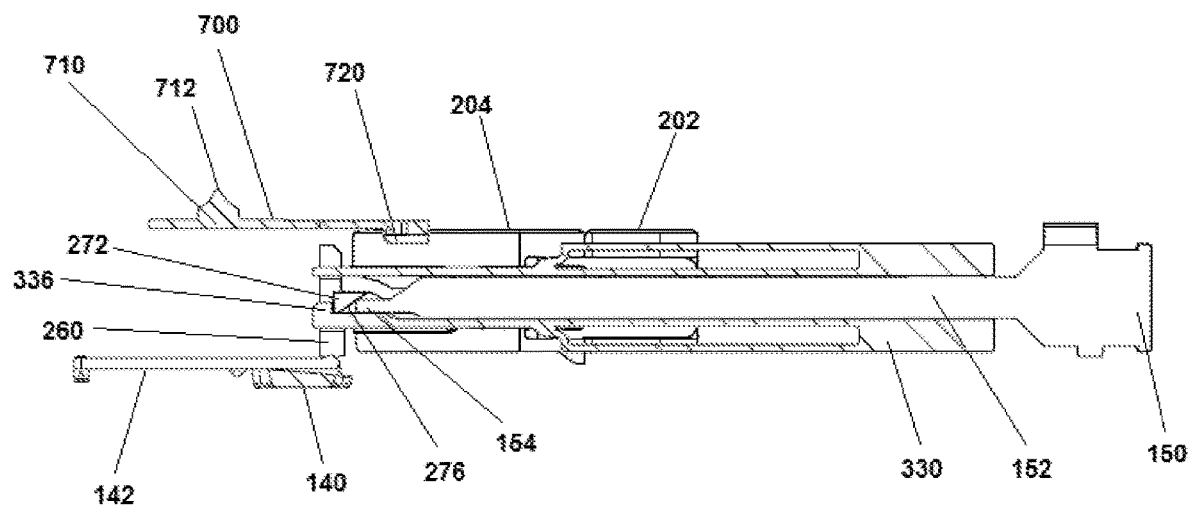
FIG. 17A is a cross-sectional view along lines A-A in FIG. 17.
Figure 17B:
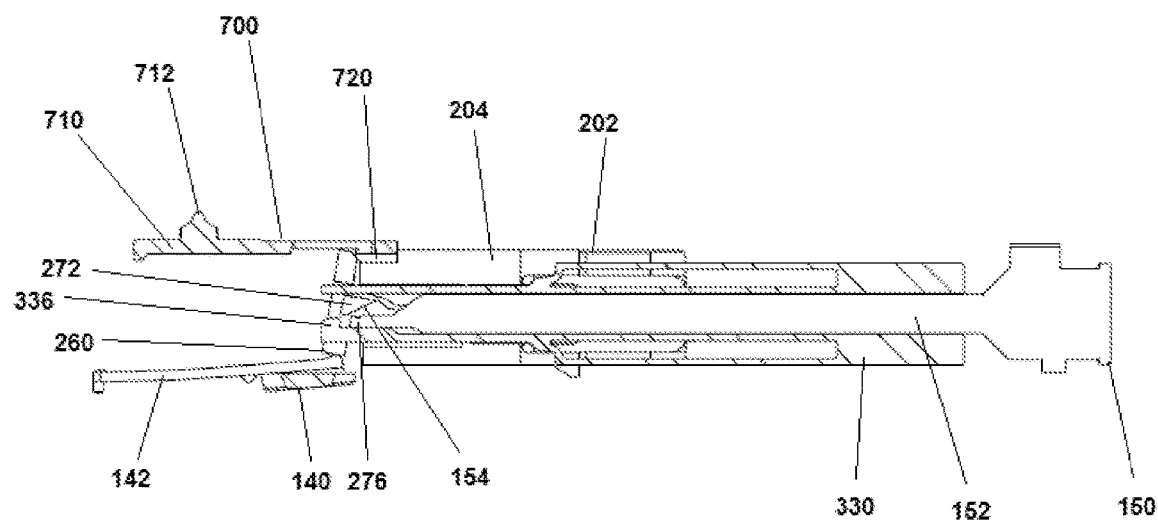
FIG. 17B is the cross-section view of FIG. 17A, showing the device being fired by depressing the side button.
Figure 17C:
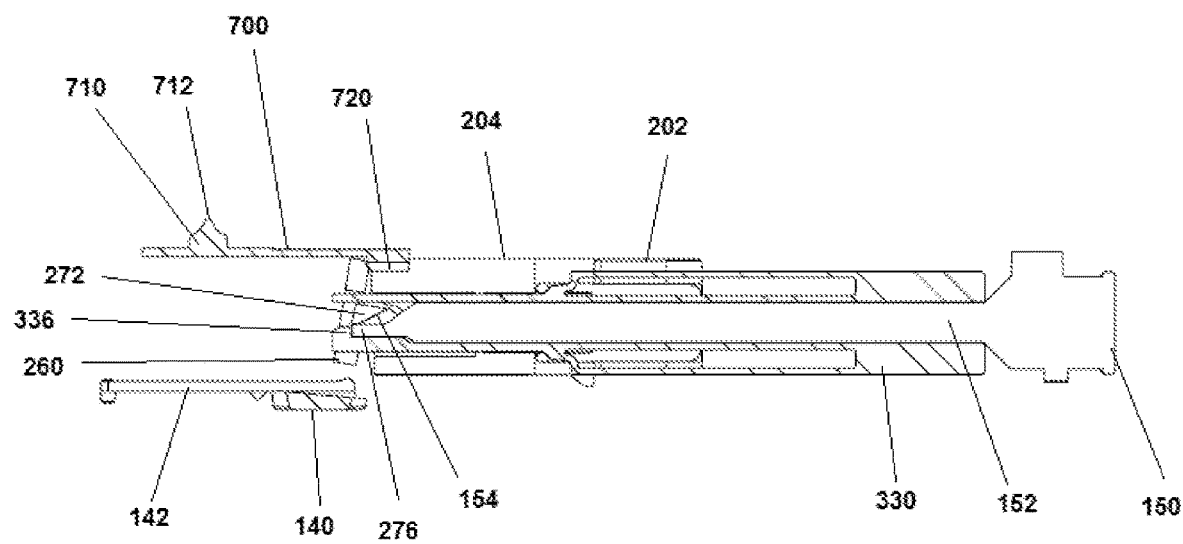
FIG. 17C is the cross-section view of FIG. 17A, showing the device being fired by depressing the rear button.
Figure 18:
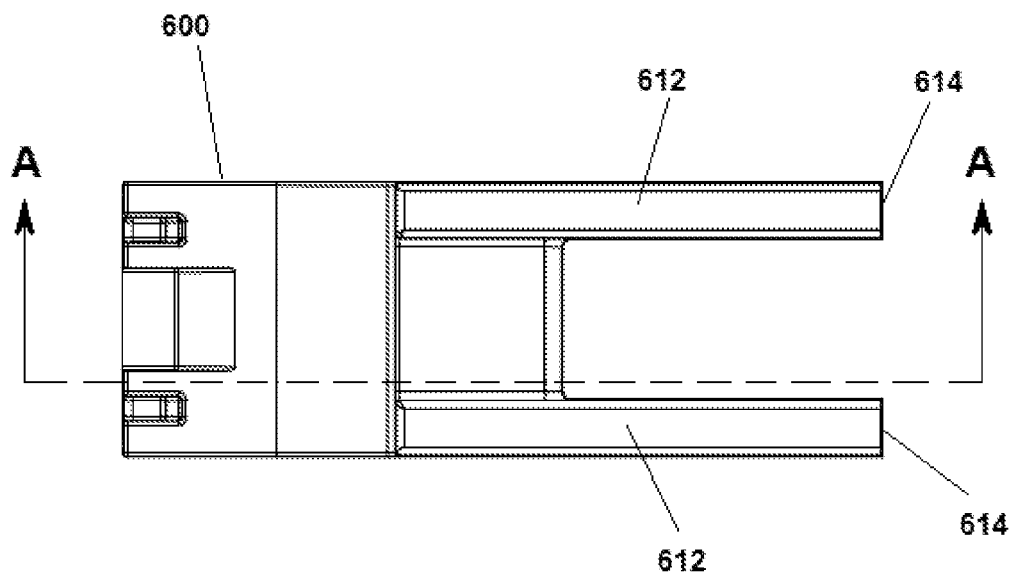
FIG. 18 is a top view of the stroke adjuster according to one embodiment of the present invention.
Figure 18A:
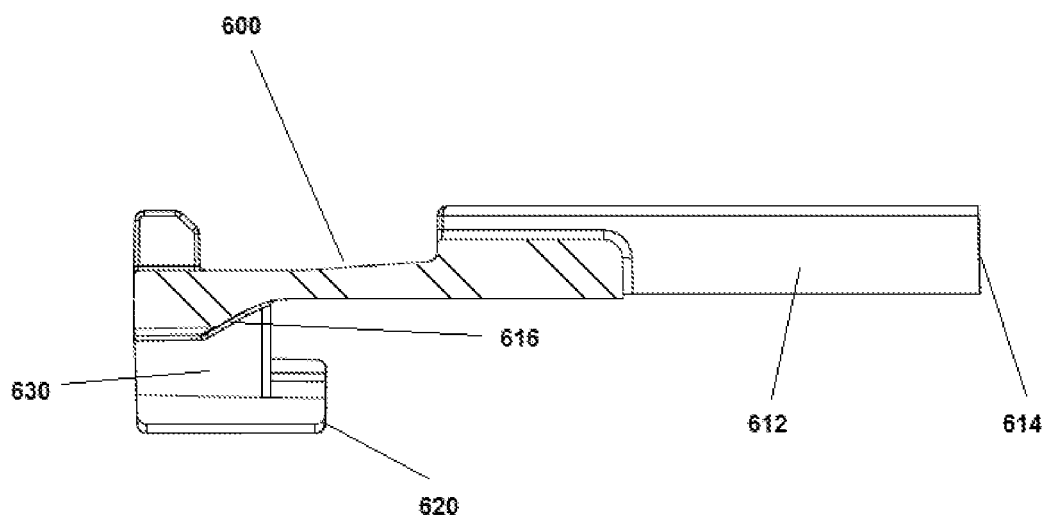
FIG. 18A is a cross-sectional view along lines A-A in FIG. 18.

As shown in FIG. 8, the front carriage 204 includes a deflecting portion 260 extending proximally from the main body of the front carriage 204. The deflecting portion 260 may be integral with the main body of the front carriage 204, and defined by cutouts 262, 264 on either side of the deflecting portion 260. In a neutral position 902, the deflecting portion 260 is substantially aligned with the longitudinal axis, as shown in FIG. 17A. In a deflected position 904, the deflecting portion 260 is flexed at an angle to the longitudinal axis, as shown in FIGS. 17B and 17C.

In the embodiment shown in FIG. 8, the deflecting portion 260 is generally T-shaped and comprises a bar 266 and a flexible beam 268. The flexible beam 268 may be asymmetrical with respect to the longitudinal axis, in order to provide greater deflection in one direction than in the other.

In a preferred embodiment, the deflecting portion 260 deflects toward cutout 262 and away from cutout 264. In that embodiment, cutout 262 is preferably wider at the distal end to accommodate the deflecting portion 260 as it is deflected transversely.

The deflecting portion 260 is further provided with a post 272 extending upwardly. The post 272 has a width less than the width of the channel 334 and is configured to fit within the channel 334 when the catcher 330 is placed on top of the front carriage 204. Preferably, the height of the post 272 is less than or equal to the first depth of the channel 334.

FIGS. 12A and 13A show movement of the lever assembly 300. Prior to arming the device 10, the catcher 330 is positioned proximally relative to the front carriage 204. The carriage assembly 200 is omitted from FIGS. 12A and 13A in order to provide a clearer view of the lever assembly 300 relative to the housing 100. When the lever 310 is lifted, the linkage 320 is forced to pivot and drive the foot 326 distally. Because the foot 326 rests on the footplate 332 of the catcher 330, the distal motion also causes the catcher 330 to slide distally inside of the housing 100. As the catcher 330 is advanced distally over the front carriage 204, the post 272 is slidably received within the channel 334. With the deflecting portion 260 of the front carriage 204 in the neutral position 902, the catch 336 overlaps at least a portion of the post 272, preventing the front carriage 204 from sliding distally with respect to the catcher 330.

As the lever 310 is closed, the pivot of the linkage 320 is reversed, causing the catcher 330 to slide proximally with respect to the housing 100. Because the catch 336 retains the post 272, the retraction of the catcher 330 also causes the carriage assembly 200 to be retracted, compressing the first biasing element 400. When the lever 310 is completely closed, the catcher 330 and carriage assembly 200 are completely retracted, and the device is in an armed state.

To fire the armed device, the deflecting portion 260 of the front carriage 204 is moved from the neutral position 902 to the deflected position 904, wherein the post 272 is moved out of longitudinal alignment with the catch 336 as shown in FIGS. 17B and 17C. When the post 272 is misaligned, the catch 336 no longer retains the post 272, and the carriage assembly 200 is free to slide distally with respect to the catcher 330 as the first biasing element 400 decompresses. In at least one embodiment, the width of the post 272 is less than or equal to the width of the channel 334 minus the width of the catch 336, such that the post 272 may pass through the space formed by the catch 336 and channel 334. When the post 272 has advanced distally past the catch 336, the beam 268 unflexes and the deflecting portion 260 returns to the neutral position 902.

It can be appreciated in alternative embodiments that the beam 268 may be oriented at an angle to the longitudinal axis in the neutral position 902. In those embodiments, the catch 336 still overlaps the post 272 in the neutral position 902 in a longitudinal direction, the post 272 is deflected into the channel and away from the catch 335 when in the deflected position 904.

To move from the neutral position 902 to the deflected position 904, the deflecting portion is provided with a transverse face 274 and an inclined face 276. The transverse face 274 is substantially parallel to the longitudinal axis of the device 10. When a transverse force is applied to the transverse face 274, the beam 268 bends generally in the direction of the transverse force. A side button 140 may be disposed in a side of the housing 100 and is depressible into the device 10 to apply a transverse force to the transverse face 274 as shown in FIG. 17B. In other embodiments, the transverse force may be applied by a different activating element, such as a switch or slide. In still further embodiments, the housing 100 may simply include an opening through which a user may directly apply a transverse force to the transverse face 274 using a finger or tool. The side button 140 may be attached to an interior wall of the housing 100 by a pair of flexible arms 142 to provide resiliency. In other embodiments, the side button 140 may include a biasing means, such as a helical spring, disposed between the side button 140 and the interior of the housing 100 to provide resiliency.

The inclined face 276 is located on the post 272 and is angled between the longitudinal and lateral axes. When a longitudinal force is applied to the inclined face 276, the beam 268 bends away from the longitudinal axis. In the embodiment illustrated in FIG. 17C, the force is applied by an elongated pusher 152 extending distally from a rear button 150 disposed in a proximal end of the housing 100. The pusher 152 is dimensioned to be slidable within the space defined by the channel 334 and the top surfaces of the carriages 202, 204, and preferably has a width less than or equal to the width of the channel 334 and a height less than or equal to the first depth of the channel 334. As the distal end of the pusher 152 is pushed against the inclined face 276, a transverse force is applied to the post 272, causing the deflecting portion 260 to deflect transversely. The rear button 150 may be attached to an interior wall of the housing 100 by a pair of flexible wings 156 to provide resiliency. In at least one embodiment, the flexible arms wings 156 are connected to arm rests 144. In other embodiments, the rear button 150 may include a biasing means, such as a helical spring, disposed between the rear button 150 and the interior of the housing 100 to provide resiliency. In a preferred embodiment, the rear button 150 may be depressed approximately 3 mm into the housing 100.

In the embodiment pictured in FIG. 17C, the pusher 152 is approximately as wide as the channel 334 in order to stabilize the pusher 152 as it is advanced longitudinally. The distal tip 154 of the pusher 152 may have a width less than a lateral width of the inclined face 276, in order to wedge between the inclined face 276 and a wall of the channel 334. In other embodiments, the distal tip 154 of the pusher 152 may be wider than the inclined face 276. In a further preferred embodiment, the width of the channel 334 is greater than or equal to the width of the distal tip 154 plus the width of the post 272, such that the distal tip 154 and post 272 may fit side-by-side within the channel 334 when the distal tip 154 is in contact with the catch 336.

In the embodiment pictured in FIG. 17C, the distal tip 154 terminates in flat face normal to the longitudinal axis. However, the distal tip 154 and inclined face 276 may be configured in a variety of shapes to produce a transverse force on the deflecting portion 260. In some embodiments, the inclined face 276 may be normal to the longitudinal axis, while the distal tip 154 is provided with a sharply angled tip. In other embodiments, the inclined face 276 or the distal tip 154 or both may be provided with curved surfaces.

Because the catcher 330 is used to retain the carriage assembly 200 in an armed state, the catcher 330 must remain proximally retracted until firing. In one embodiment shown in FIGS. 21, 22, and 22A, the device 10 is provided with a lockout assembly 500 in order to prevent the lever 310 from being operated and inadvertently advancing the catcher 330 when the device is in an armed state. The lockout assembly 500 comprises a blocker 510, a lever release 520 and a second biasing element 530.

The lever release 520 comprises a slidable switch 522 disposed in a side of the housing 100 and a latch 524 to engage the lever 310. In the embodiment shown in FIG. 22A, the latch 524 is a proximally facing protrusion that engages a ledge 314 on the underside of the lever 310. The latch 524 may be released by sliding the lever release 520 distally off of the ledge 314. The lever release 520 is biased proximally by the second biasing element 530 to keep the latch 524 engaged with the lever 310 when the lever release 520 is not being operated.

The lever release 520 may optionally be provided with an inclined surface 526, which engages an abutment 316 on the underside of the lever 310. When the lever release 520 is advanced distally, the inclined surface 526 contacts the abutment 316 and drives the lever 310 upward away from the device 10. It is believed that the separating action of the lever release 520 enables a user to more easily grasp the lever 310. In some embodiments, the slidable switch 522 may be a generally rectangular extrusion having a flat face, although other shapes are within the scope of invention. In other embodiments, the slidable switch 522 may include a raised portion 528 on one side and the face may be sloping or curved. It is believed that the raised portion 528 facilitates movement of the slidable switch 522 using the thumb or a single finger.

Figure 21:
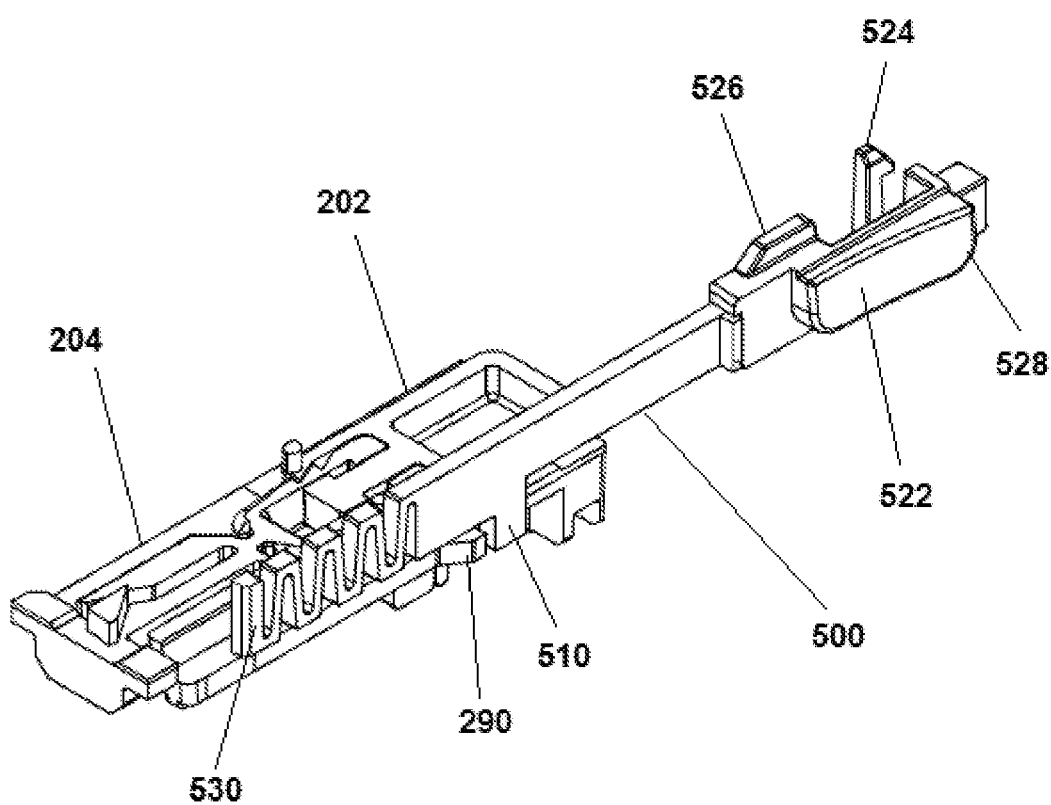
FIG. 21 is a perspective view of the carriage assembly and lockout assembly according to one embodiment of the present invention.

The blocker 510 may be a protuberance extending downwardly to engage a side tab 290 extending from the front carriage 204, as illustrated in FIG. 21. When the device is not armed, the front carriage 204 is positioned near a distal end of the housing 100. In that position, the side tab 290 is located distally of and separated from the blocker 510. Because the blocker 510 and side tab 290 are separated, the lever release 520 may be operated, compressing the second biasing element 530 and advancing the blocker 510 distally. After the device is armed, the front carriage 204 is retracted proximally, and the side tab 290 abuts the blocker 510. In that position, the blocker 510 is prevented from advancing distally by the side tab 290. Consequently, the second biasing element 530 cannot be compressed and the lever release 520 cannot be advanced. Because the lever release 520 remains biased proximally, the latch 524 cannot be disengaged from the ledge 314, and the lever 310 cannot be operated.

In other embodiments, a side tab 292 may extend from the rear carriage 202, and the side tab 292 of the rear carriage abuts the blocker 510 in the same manner as above. In embodiments comprising only a singular carriage, a side tab 294 may extend from the single carriage, and the side tab 294 of the singular carriage abuts the blocker 510 in the same manner as above.

Figure 22:
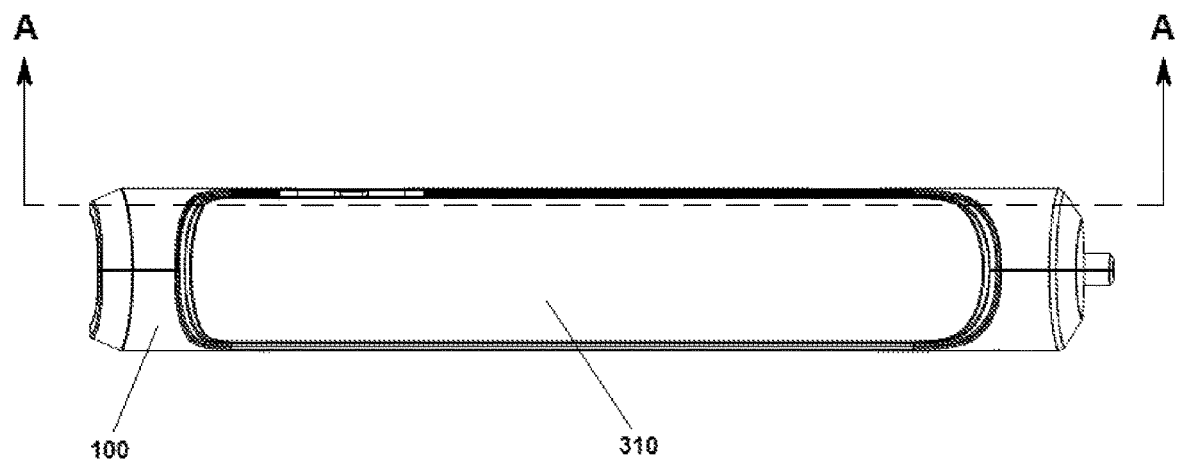
FIG. 22 is a top view of the lever, lockout assembly, and housing according to one embodiment of the present invention.
Figure 22A:
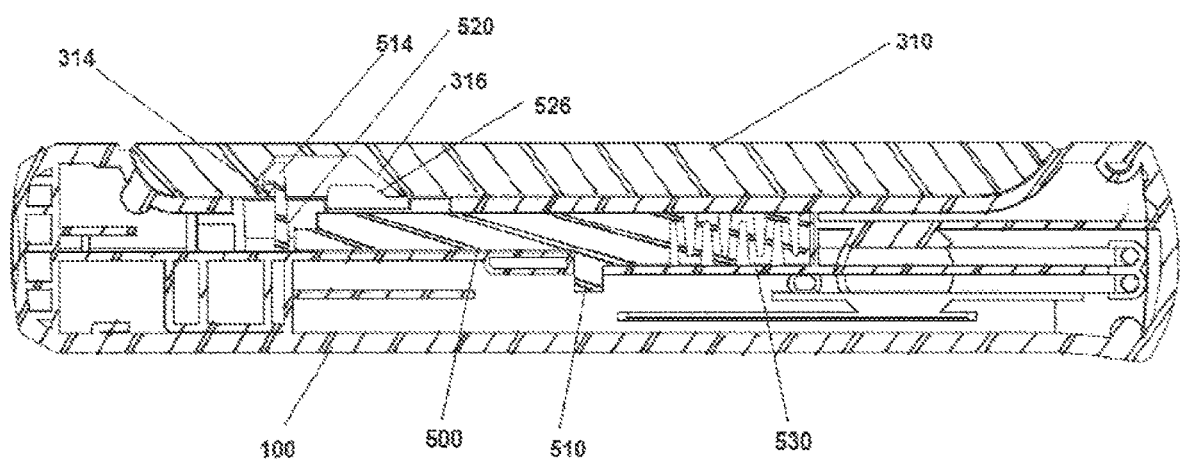
FIG. 22A is a cross-sectional view along lines A-A in FIG. 22.

In the embodiment depicted in FIGS. 21-22, the second biasing element 530 is integral with the lockout assembly 500 and is generally sinusoidal in shape. In other embodiments, the second biasing element 530 may be separately formed and may be any compressible element, including a helical spring. In further embodiments, the lever release 520 may be integral with the lockout assembly 500.

In at least one embodiment, the device is provided with a safety mechanism 700. As illustrated in FIGS. 16, 16A, 17, and 17A-C, the safety mechanism 700 comprises a safety switch 710 disposed in the side of the housing 100 and an obstructer 720 extending into the housing 100. The safety mechanism 700 is slidable between a locked state 912 and an unlocked state 914. In the locked state 912, the obstructer 720 is positioned between the deflecting portion 260 and an interior wall 730 of the housing 100, preventing the deflecting portion 260 from being deflected toward the interior wall 730. When the safety mechanism 700 is moved to the unlocked state 914, the obstructer 720 is moved out of position between the interior wall 730 and the deflecting portion 260, and the deflecting portion 260 is free to deflect toward the interior wall 730.

When the safety mechanism 700 is in the locked state 912, the obstructer 720 preferably extends from the interior wall 730 and contacts a face of the deflecting portion 260 in its neutral position 902. In other embodiments, however, the obstructer 720 may be shorter to allow a small degree of deflection where the catch 336 of the catcher 330 and the post 272 of the front carriage 204 are still substantially aligned.

In some embodiments, the safety 700 may include a flexible spring arm 740. The spring arm 740 extends longitudinally and includes a bump 742 to engage one of a pair of detents 180 on an interior wall of the housing 100. In a neutral position, the projection is engaged into one of the two detents. As sufficient longitudinal force is applied to the safety 700, the bump 742 is pushed out of the detent 180 and the spring arm 740 flexes slightly against the housing 100. When the spring arm 740 reaches the other detent 180, the bump 742 engages the detent 180, and the spring arm 740 returns to a neutral position.

In the embodiments shown in FIGS. 16, 16A, 17, and 17A-C, the safety switch 710 is oriented longitudinally and positioned near the distal end of the housing 100. In other embodiments, however, the safety switch 710 may be rotated with respect to the lateral axis or repositioned on the housing 100 so that the obstructer 720 prevents flexing of the deflecting portion 260 in the locked state 912. In further embodiments, the safety switch 710 may be an elliptical extrusion having a flat face, although other shapes are within the scope of invention. In still further embodiments, the safety switch 710 may include a crest 712 transverse to the direction of movement and having sloping or concave sides. It is believed that the crest 712 facilitates movement of the safety switch 710 using the thumb or a single finger.

Figure 4:
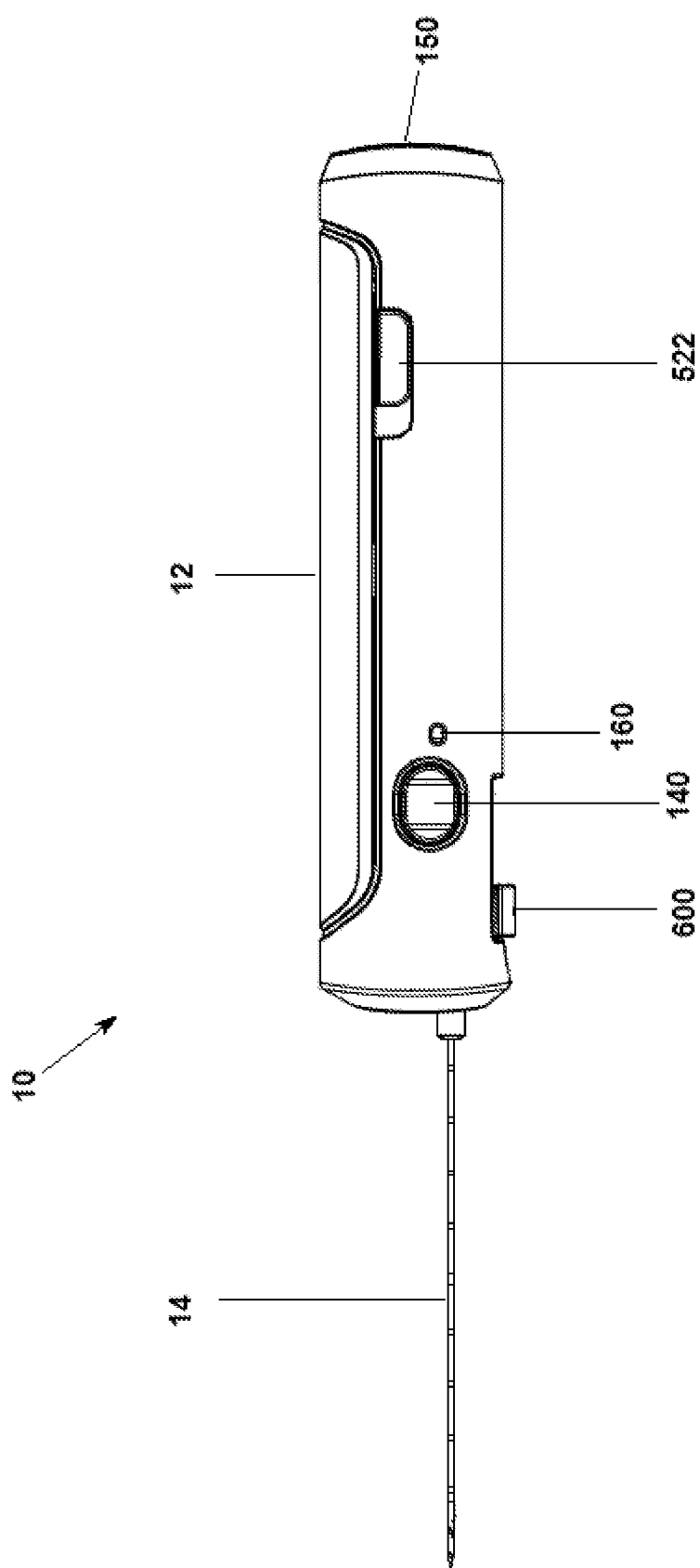
FIG. 4 is a right side view of the biopsy device handle and needle of FIG. 1
Figure 5:
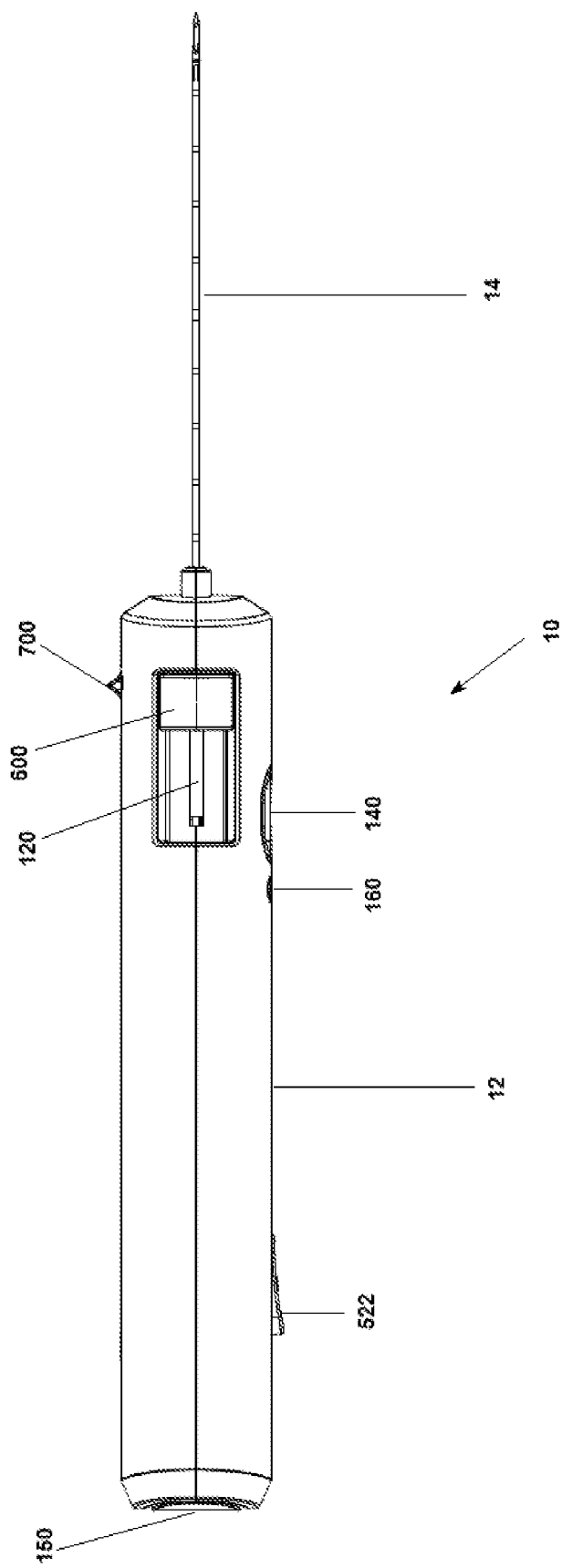
FIG. 5 is a bottom view of the biopsy device handle and needle of FIG. 1
Figure 6:
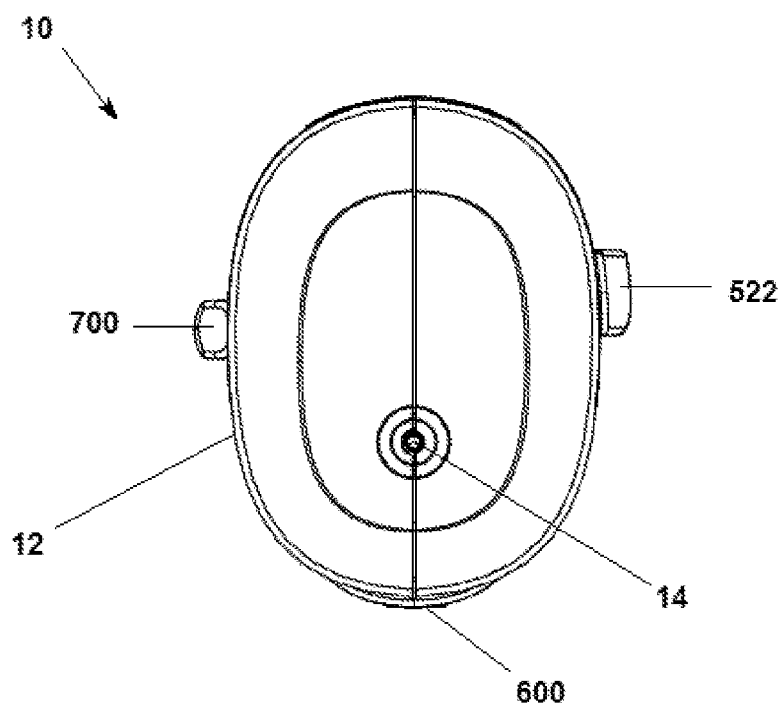
FIG. 6 is a front view of the biopsy device handle and needle of FIG. 1
Figure 7:
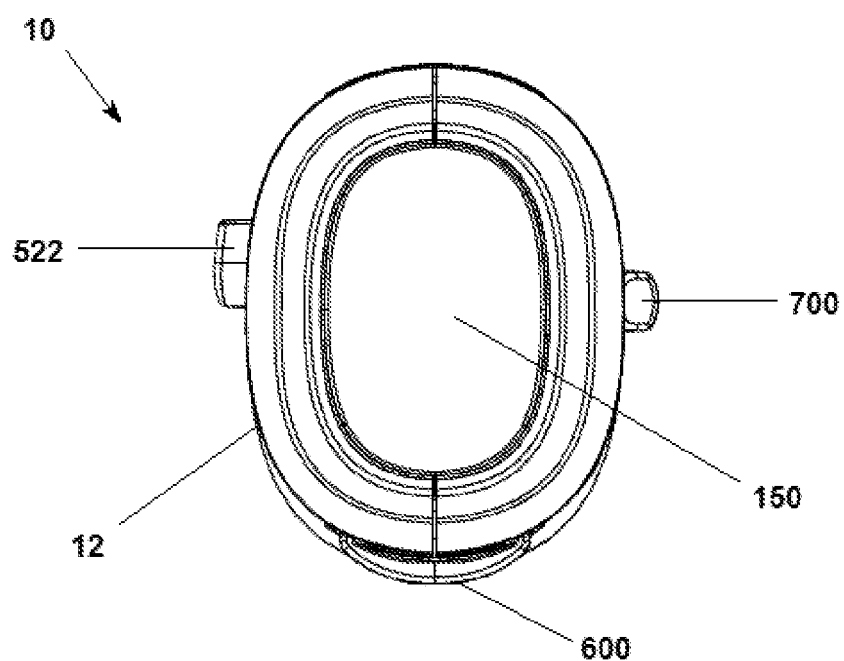
FIG. 7 is a rear view of the biopsy device handle and needle of FIG. 1

The housing 100 may be further provided with an indicator window 160, as shown in FIG. 4, through which a portion of the rear or front carriage 202, 204 is visible when the device is in an armed state and not visible through the window 160 when the device is in any other state. Preferably, the visible portion of the carriage 202, 204 is provided with a marking, such as a contrasting coloration, a painted symbol, or etching.

Although the present invention has been described in relation to particular embodiments thereof, it can be appreciated that other variations and modifications will be apparent to those skilled in the art without departing from the teaching of the invention. Therefore, the present invention is not limited by the specific disclosure herein but only by the claims.

The invention claimed is:

1. A biopsy device handle comprising:
an elongated housing, the length of the housing defining a longitudinal axis;
a carriage disposed within the housing and having a flexible abutment;
a catch overlapping at least a portion of the abutment in a longitudinal direction;
a first trigger disposed in the housing and movable longitudinally within the housing and contacting a portion of the flexible abutment wherein longitudinal movement of the first trigger causes a first contact force to be applied to the abutment;
a second trigger disposed in the housing and movable transversely within the housing and contacting a portion of the flexible abutment wherein transverse movement of the second trigger causes a second contact force to be applied to the abutment;
wherein the abutment is configured to flex away from the catch when forced by either the first or second contact force, such that the catch does not overlap a portion of the abutment.

2. The biopsy device handle of claim 1, wherein the carriage is configured to slide longitudinally within the housing and the catch is disposed distally of the abutment when the catch is overlapping the abutment.

3. The biopsy device handle of claim 2, wherein the carriage is biased in a distal direction by a biasing element.

4. The biopsy device handle of claim 1, wherein the first trigger is a button disposed in an end of the housing and configured to depress into the housing.

5. The biopsy device handle of claim 1, wherein the second trigger is a button disposed in a side of the housing and configured to depress into the housing.

6. The biopsy device handle of claim 1, wherein the flexible abutment includes an inclined face at an angle to the longitudinal axis, the angled face deflecting at least partially in a transverse direction when a longitudinal force is applied to the angled face.

7. The biopsy device handle of claim 6, wherein the inclined face is on a post extending from the abutment.

8. The biopsy device of claim 1, wherein the abutment is generally T-shaped.

9. The biopsy device handle of claim 3, wherein the biasing element forces the carriage in a distal direction when the abutment is flexed away from the catch.

10. The biopsy device handle of claim 1, further including a channel having first and second opposing walls, wherein the catch extends inwardly from the first wall of the channel.

11. The biopsy device handle of claim 10, wherein the abutment is flexed between the catch and the second wall of the channel.

12. The device of claim 11, further comprising a switch on a side of the housing, the switch having an internal protrusion extending transversely within the housing and configured to slide longitudinally between a first position and a second position;
wherein the internal protrusion is disposed between an interior wall of the housing and the abutment in the first position, and the internal protrusion is misaligned with the abutment in the second position.

13. The biopsy device of claim 1, further comprising a first biasing element disposed between a proximal end of the housing and the carriage and configured to bias the carriage in a distal direction, a lever operatively linked to the catch, a latch configured to slide longitudinally to releasably engage the lever in a proximal direction and a second biasing element disposed distally of the latch and configured to bias the latch in a proximal direction; wherein the lever is configured to move the catch distally of the abutment when opened and move the catch in a proximal direction when closed; and wherein the catch is configured to engage the abutment when the catch is moved in the proximal direction such that the carriage is forced against the first biasing element; and wherein the latch further includes a blocker configured to engage a proximal face of the carriage such that the latch is prevented from moving distally when the carriage is moved to a proximal position.

* * * * *